United States Patent [19]

Stolowitz et al.

[11] Patent Number: 6,124,471
[45] Date of Patent: Sep. 26, 2000

[54] PHENYLDIBORONIC ACID REAGENTS AND COMPLEXES

[75] Inventors: Mark L. Stolowitz, Woodinville; Edward A. Kesicki, Bothell; Kevin P. Lund, Lynnwood; Karin A. Hughes, Bothell, all of Wash.

[73] Assignee: Prolinx, Inc., Bothell, Wash.

[21] Appl. No.: 09/407,673

[22] Filed: Sep. 28, 1999

Related U.S. Application Data

[60] Division of application No. 09/138,105, Aug. 21, 1998, which is a continuation-in-part of application No. 08/689,283, Aug. 5, 1996, Pat. No. 5,837,878, and a continuation-in-part of application No. 08/689,341, Aug. 5, 1996, Pat. No. 5,847,192.

[51] Int. Cl.$^7$ ........................................ C07F 5/02
[52] U.S. Cl. .............................. 548/405; 558/290; 562/7
[58] Field of Search .................. 562/7; 548/405; 558/290

[56] References Cited

U.S. PATENT DOCUMENTS

| | | | |
|---|---|---|---|
| 2,548,257 | 7/1951 | Goldberg et al. | 562/453 |
| 4,269,605 | 5/1981 | Dean et al. | 436/67 |
| 4,281,181 | 7/1981 | Nagasawa et al. | 562/453 |
| 4,496,722 | 1/1985 | Gallop et al. | 544/69 |
| 4,713,346 | 12/1987 | Gallop et al. | 436/86 |
| 4,783,487 | 11/1988 | Brune | 514/563 |
| 4,851,443 | 7/1989 | Brune | 514/563 |
| 4,894,229 | 1/1990 | Polson et al. | 424/92 |
| 4,910,300 | 3/1990 | Urdea et al. | 536/287 |
| 5,002,883 | 3/1991 | Bieniarz et al. | 435/176 |
| 5,045,451 | 9/1991 | Uhr et al. | 435/6 |
| 5,093,232 | 3/1992 | Urdea et al. | 435/7.23 |
| 5,183,653 | 2/1993 | Linder et al. | 424/1.1 |
| 5,464,861 | 11/1995 | Dobrusin et al. | 514/414 |

FOREIGN PATENT DOCUMENTS

| | | |
|---|---|---|
| 9013818 | 11/1990 | WIPO . |
| 9208722 | 5/1992 | WIPO . |
| 9420858 | 9/1994 | WIPO . |

OTHER PUBLICATIONS

Wilcheck, M. & Bayer, E.A.;"Introduction to Avidin–Biotin Technology"; *Methods in Enzymology*; vol. 184; 1990 (USA).

Kessler et al.;"Non–radioactive Labeling and Detection of Nucleic Acids"; *Biol. Chem. Hoppe–Seyler*; vol. 371, pp. 917–927; 1990 (USA).

Singhai, R.P. & DeSilva, S.S.M.; "Boronate Affinity Chromatography"; *Advances in Chromatography*; vol. 31, pp. 293–335; 1992 (USA).

Mazzeo, J.R. & Krull, I.S.; "Immobilized Boronates for the Isolation and Separation of Bioanalytes"; *Biochromatography*; vol. 4, pp. 124–130; 1989.

Bergold, A. & Scouten, W.H.; "Borate Chromatography"; *Solid Phase Biochemistry*; Ch. 4, pp. 149–187;1983 (USA).

Lorand, J.P. & Edwards. J.O.;"Polyol Complexes and Structure of the Benzeneboronate Ion"; *J. Org. Chem.*; vol. 24, p. 769; 1959 (USA).

Bowie, R.A. & Musgrave, O.C.; "Organoboron Compounds. Part V.* The Hydrolysis of Cyclic Phenylboronates"; *J. Amer. Chem. Soc.*; pp. 3945–3949; 1963 (USA).

Sienkiewicz, P.A. & Roberts, D.C.; "pH Dependence of Boronic Acid–Diol Affinity in Aqueous Solution"; *J. Inorg. Nucl. Chem.*; vol. 42, pp. 1559–1571; 1980 (USA).

Tanner, D.W. & Bruice, T.C.; "Boric Acid Esters" *J. Amer. Chem. Soc.*; vol. 89, pp. 6954–6971; 1967 (USA).

Kliegel, W. & Nanninga, D.; "Borchelate von Salicylaldoxim und Derivaten"; *Monatshefte Fur Chemie*; vol. 114, pp. 465–484; 1983 (FRG).

Imagawa et al.; "Characteristics and Evaluation of Antibody–Horseradish Peroxidase Conjugates, etc."; *J. Applied Biochemistry*; vol. 4, pp. 41–57; 1982 (USA).

Kessler, C.; *Advances in Mutagenesis Research* (Obe, G. ed.); pp. 105–152; Springer–Verlag, Berlin/Heidelberg; 1990 (USA).

(List continued on next page.)

*Primary Examiner*—Richard Raymond
*Attorney, Agent, or Firm*—Blakely, Sokoloff, Taylor & Zafman

[57] ABSTRACT

Reagents suitable for the modification of a bioactive species for the purpose of incorporating one or more phenyldiboronic acid (PDBA) moieties for subsequent conjugation to a different (or the same) bioactive species having one or more pendant boronic compound complexing moieties of the general formula of General Formula I,

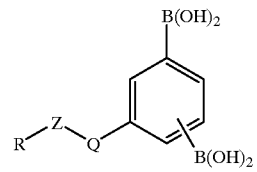

General Formula I wherein group R is a reactive electrophilic or nucleophilic moiety suitable for reaction of the PDBA reagent with a bioactive species. Group Z is a spacer selected from a saturated or unsaturated chain up to about 0 to 6 carbon equivalents in length, an unbranched saturated or unsaturated chain of from about 6 to 18 carbon equivalents in length with at least one intermediate amide or disulfide moiety, and a polyethylene glycol chain of from about 3 to 12 carbon equivalents in length. Group Q is a linkage that includes one of amide, ether and thioether moieties. Group R is preferably selected from, but not limited to, one of acrylamide, bromo, bromoacetamide, chloro, chloroacetamide, dithiopyridyl, hydrazide, N-hydroxysuccinimidyl ester, N-hydroxysulfosuccinimidyl ester, imidate ester, imidazolide, iodo, iodoacetamide, maleimide, amino and thiol moieties. Group Z is preferably an unbranched alkyl chain of the general formula $(CH_2)n$, wherein n=1 to 6. Group Q is preferably selected from one of NHCO, CONH, $NHCOCH_2$, $CONHCH_2$, O, $OCH_2$, S and $SCH_2$ moieties.

4 Claims, 9 Drawing Sheets

OTHER PUBLICATIONS

Brinkley, M.; "A Brief Survey of Methods for Preparing Protein Conjugates with Dyes, Haptens, and Cross Linking Reagents"; *Bioconjugate Chem.*; vol. 3, pp. 2–13; 1992 (USA).

Linder et al.; "Technetium Labeling of Monoclonal Antibodies with Functionalized BATOs 1. TcCl(DMG)$_3$PITC"; *Bioconjugate Chem.*; vol. 2, pp. 160–170; 1991 (USA).

Linder et al.;"Technetium Labeling of Monoclonal Antibodies with Functionalized BATOs 2. TcCl(DMG)$_3$CPITC Labeling of B72.3, etc." *Bioconjugate Chem.*; vol. 2, pp. 407–415; 1991 (USA).

Burnett et al.;"Synthesis of a Fluorscent Boronic Acid Which Reversibly Binds to Cell Walls, etc."; *Biochem. Biophys. Research Commun.*; vol. 96, pp. 157–162; 1980 (USA).

Steinberg, G.M. & Swidler, R.; "The Benzohydroxamate Anion"; *J. Org. Chem.Vol.* ; vol. 30, pp 2362–65; 1965 (USA).

Bauer, L. & Exner, O.; "The Chemistry of Hydroxamic Acids and N–Hydroxyimides"; *Angew. Chem. Internat. Edit.*; vol. 13, pp. 376–384; 1974 (USA).

Cai, S.X. & Kean, J.;"o –Acetomidophenylboronate Esters Stabilized Toward Hydrolysis by an Intramolecular O–B Interation, etc."; *Bioconjugate Chem.*; vol. 2, pp 317–22; 1991 (USA).

Ramalingam, K. & Nowotnik, D.; "Syntheses of Some Isothiocyanatophenylboronic Acids"; *Org. Prep. Proc. Int.*; vol. 23, 729–34; 1991 (USA).

Kliegel, W. & Nanninga, D.; "Borchelate Von Salicyladehydnitronen"; *Journal of Organometallic Chem.*; vol. 243, pp 373–85; 1983 (USA).

Ripan et al.; "Etude Du Systeme Acide Borique–Salicylaldoxime en Solutions Aqueuses"; *Revue Roumaine de Chimie*; vol. 10, pp 965–71; 1965 (FRA).

Roberts et al.; "Pluripotential Amino Acids"; *Tetrahedron Letters*; vol. 21, pp. 3435–3438; 1980 (USA).

Kemp, D.S. & Roberts, D.;"New Protective Groups for Peptide Synthesis—II the DOBZ Group, etc."; Tetrahedron Letters; vol. 52, pp. 4629–4632; 1975 (USA).

Kliegel, W. & Nanninga, D.;"Borchelate von N–substituierten Hydroxamsauren"; *Chem. Ber.*; vol. 116, pp. 2616–2629; 1983 (FRG).

Mikesova, M. & Bartusek, M.;"Reaction of Boric Acid with Salicylic and Chromotropic Acids and with Their Derivatives"; *Chem. Zvesti*; vol. 32(4), pp. 472–477; 1978.

Feeney, R.E., "Chemical Modification of Proteins; Comments and Perspectives"; *Int. J. Peptide Protein Res.*; vol. 29, pp. 145–161 (USA), 1987.

Means, G.E. & Feeney, R.E.; "Chemical Modifications of Proteins: History and Applications"; *Bioconjugate Chem.*; vol. 1, pp. 2–12 (USA), 1990.

O'Shannessy, D.J. & Quarles, R.H.; "Labeling of the Oligosaccharide Moieties of Immunoglobulins"; *J. Immunological Methods*; vol. 99, pp 153–61 (1987) (USA).

van't Reit, B., Wampler, G.L., & Elford, H.L.; "Synthesis of Hydroxy– and Amino– Substituted Benzohydroxamic Acids, etc."; *J. Medicinal Chem.*; vol. 22. No. 5, 589–92 1979 (USA).

Soundararajan, et al.; "Boronic Acids for Affinity Chromatography; Spectral Methods for Determination, etc."; *Analytical Biochem.*; vol. 178, pp. 125–134, 1989 (USA).

Goodchild, J.; "Conjugates of Oligonucleotides and Modified Oligonucleotides: A Review of Their Synthesis and Properties"; *Bioconjugate Chem.*; vol. 1, No. 3, pp. 165–193, 1990 (USA).

Kessler, C.; *Nonradioactive Labeling and Detection of Biomolecules*; Ch. 1–3, 1992 (USA).

Meares, C.F., "Editorial: Introduction to Bioconjugate Chemistry"; *Bioconjugate Chem.*; vol. 1, No. 1, 1990 (USA).

Waggoner, A.S.; "Fluorescent Probes for Cytometry"; *Flow Cytometry and Sorting*; 2nd ed; pp. 209–225; 1990 (USA).

Borrebaeck, C.;"Strategy for the production of human monoclonal antibodies using in vitro activated B cells"; *J. Immun. Methods*; vol. 123; 157–65; 1989 (USA).

Chen, et al.; "Structure–Activity Relationships in a Series of 5–[(2,5–Dihydroxybenzyl) amino]salicylate, etc."; Chemical Abstracts; vol. 120; 322877v; 1994 (USA).

Hirano, et al.; "Silver halide color photographic material"; Chemical Abstracts; vol. 116; 140012u; 1992 (USA).

Kawasaki, et al.; "Silver halide photographic material with improved storage stability"; Chemical Abstracts; vol. 109; 160505r; 1988 (USA).

Priewe, H., et al.; "o–Hydroxybenzohydroxamic Acids"; Chemical Abstracts; vol. 52; 10184; 1958 (USA).

Regnier, G., et al., No. 473–"Acide–Phenols", Bulletin de la Societe Chimique de France 1966, No. 9, pp. 2821–2827.

Meindl, W., et al.; "Antimykobakterielle N–Alkylbenzylamine", Arch. Pharm., 315, 941–46 (1982).

Thompson, A.M., et al.; Tyrosine Kinase Inhibitors; Synthesis of 2,2'–Dithiobis (1H–indole–3–alkanamides) and Investigation of Their Inhibitory Activity against Epidermal (cont.) Growth Factor Receptor and pp60$^{vsrc}$ Protein Tyrosine Kinases, J. Med. Chem., 1994, 37, 598–609.

Quelet, R., et al., No. 303–"Chloromethylation de l'acide salicylique et des ethers phenoliques correspondants", Bulletin de la Societe Chimique de France, 1969, No. 5, pp. 1698–1705.

Malmberg, H., et al.; Stereoselectivity in the transfer of the 2–(1–dimethylaminoethyl) phenyl group, R, from LiR$_2$Cu and Li(R)–(2–thienyl)Cu to enones, Chem Abstracts; vol. 98;71593e;1982.

Bailey et al., Chemical Abstracts, vol. 111, abstract 130131, 1989.

Ciba Inc., Chemical Abstracts, vol. 66, abstract 85610, 1987.

PHENYLDIBORONIC ACID REAGENTS AND COMPLEXES

CROSS-REFERENCE TO RELATED APPLICATIONS

This application is a divisional of U.S. patent application Ser. No. 09/138,105, filed Aug. 21, 1998, which is a continuation in part of U.S. patent application Ser. No. 08/689,283, filed Aug. 5, 1996 now U.S. Pat. No. 5,837,878, and a continuation in part of U.S. patent application Ser. No. 08/689,341, filed Aug. 5, 1996 now U.S. Pat. No. 5,847,192.

FIELD OF THE INVENTION

The present invention relates to the field of bioconjugate preparation, and more particularly, to a class of phenyldibronic acid (PDBA) reagents useful for the conjugation of biological macromolecules, and the method of making and using such reagents.

BACKGROUND OF THE INVENTION

Bioconjugation is a descriptive term for the joining of two or more different molecular species by chemical or biological means, in which at least one of the molecular species is a biological macromolecule. This includes, but is not limited to, conjugation of proteins, peptides, polysaccharides, hormone, nucleic acids, liposomes and cells, with each other or with any other molecular species that add useful properties, including, but not limited to, drugs, radionuclides, toxins, haptens, inhibitors, chromophores, fluorophores, ligands, etc. Immobilization of biological macromolecules is also considered a special case of bioconjugation in which the macromolecule is conjugated, with reversibly or irreversibly, to an insoluble support including a chromatographic support. Bioconjugation is utilized extensively in biochemical, immunochemical and molecular biological research. Major applications of bioconjugation include, but are not limited to, detection of gene probes, enzyme-linked immunological solid-phase assay, monoclonal antibody drug targeting and medical imaging.

Bioconjugates are generally classified as either direct or indirect conjugates. Direct conjugates encompass those in which two or more components are joined by direct covalent chemical linkages. Alternatively, indirect conjugates encompass those in which two or more components are joined via an intermediary complex involving a biological macromolecule.

AVIDIN-BIOTIN SYSTEM

Although numerous methods of indirect bioconjugate preparation have been described, a significant number of those reported in the literature have been prepared by exploiting the Avidin-Biotin system. In the Avidin-Biotin system, the binding specificity of the protein Avidin (purified from egg white), or Streptavidin (purified from the bacterium *Streptomyces avidinii*), toward the cofactor Biotin (vitamin H) is utilized to bridge an Avidin conjugated macromolecule with a biotinylated macromolecule. Both Avidin and Streptavidin posses four Biotin binding sites of very high affinity ($K=10^{15}$ mol$^{-1}$).

The Avidin-Biotin system has been utilized extensively for enzyme-linked immunological solid-phase assay (ELISA), in which an enzyme-Avidin conjugate (useful for detection by reaction with the enzyme's substrate to afford a colored or chemiluminescent product) is employed to detect the presence of a biotinylated antibody, after first binding the antibody to an immobilized antigen or hapten. Applications of the Avidin-Biotin system number in the hundreds, and have recently been reviewed (Wilchek, M. and Bayer, E. A., (1990) *Methods in Enzymology*, 184).

Although utilized extensively, several limitations are known to be associated with the Avidin-Biotin system, which include nonspecific binding generally attributed to the basicity of the Avidin molecule, nonspecific binding attributed to the presence of carbohydrate residues on the Avidin molecule, and background interference associated with the presence of endogenous Biotin, which is ubiquitous in both eukaryotic and prokaryotic cells.

DIGOXIGENIN ANTI-DIGOXIGENIN SYSTEM

An alternative indirect bioconjugation system designed to overcome some of the limitations associated with the Avidin-Biotin system has recently been developed for the detection of gene probes by ELISA (Kessler, C., Hôltke, H. -J., Seibl, R., Burg, J. and Mühlegger, K., (1990) *Biol. Chem. Hoppe-Seyler*, 371, 917–965. This system involves the use of the steroid hapten Digoxigenin, an alkaloid occurring exclusively in Digitalis plants, and Fab fragments derived from polyclonal sheep antibodies against Digoxigenin (anti-Digoxigenin). The high specificity of the various anti-Digoxigenin antibodies affords low backgrounds and eliminates the non-specific binding observed in Avidin-Biotin systems. Digoxigenin-labeled DNA and RNA probes can detect single-copy sequences in human genomic Southern blots. The development of the Digoxigenin anti-Digoxigenin system has recently been reviewed (Kessler, C. (1990) in Advances in Mutagenesis Research (Obe, G. ed.) pp. 105–152, Springer-Verlag, Berlin/Heidelberg). The Digoxigenin anti-Digoxigenin system is the most recent representative of several hapten-antibody systems now utilized for bioconjugation.

IMMOBILIZED PHENYLBORONATES

Phenylboronic acids are known to interact with a wide range of polar molecules having certain requisite functionalities. Complexes of varying stability, involving 1,2-diols, 1,3-diols, 1,2-hydroxy acids, 1,3-hydroxy acids, 1,2-hydroxylamines, 1,3-hydroxylamines, 1,2-diketones and 1,3-diketones, are known to form with either neutral phenylboronic acid or the phenylboronate anion. Consequently, immobilized phenylboronic acids have been exploited as chromatographic supports to selectively retain, from diverse biological samples, those molecular species having the requisite functionalities. Many important biological molecules including carbohydrates, catecholamines, prostaglandins, ribonucleosides, and steroids contain the requisite functionalities, and have been either analyzed or purified in this manner. The use of phenylboronic acid chromatographic media for the isolation and separation of biological molecules has been discussed in several reviews (Singhal, R. P. and DeSilva, S. S. M. (1992) *Adv. Chromatog.*, 31, 293–335; Mazzeo, J. R. and Krull, I. S. (1989) *BioChromatog.*, 4, 124–130; and Bergold, A. and Scouten, W. H. (1983) in Solid Phase Biochemistry (Scouten, W. H. ed.) pp. 149–187, John Wiley & Sons, New York).

Phenylboronic acid, like boric acid, is a Lewis acid, and ionizes not by direct deprotonation, but by hydration to give the tetrahedral phenylboronate anion ($pK_a=8.86$). Phenylboronic acid is three times as strong an acid as boric acid. Ionization of phenylboronic acid is an important factor in complex formation, in that, upon ionization, boron changes from trigonal coordination (having average bond angles of 120° and average bond length of 1.37 angstroms) to the tetrahedrally coordinated anion (having average bond angles of 109° and average bond lengths of 1.48 angstroms).

Molecular species having cis or coaxial 1,2-diol and 1,3-diol functionalities, and particularly carbohydrates, are known to complex with immobilized phenylboronate anion, to form cyclic esters under alkaline aqueous conditions (Lorand, J. P. and Edwards, J. O. (1959) *J. Org. Chem.,* 24, 769).

Acidification of 1,2-diol and 1,3-diol complexes to neutral pH is know to release the diol containing species, presumable due to hydrolysis of the cyclic ester. Coplanar aromatic 1,3-diols, like 1,8-dihydroxynaphthalene, are known to complex even under acidic conditions due to the hydrolytic stability of six-membered cyclic boronic acid esters (Sienkiewicz, P. A. and Roberts, D. C. (1980) *J. Inorg. Nucl. Chem.,* 42, 1559–1571).

Molecular species having pendant 1,2-hydroxylamine, 1,3-hydroxylamine, 1,2-hydroxyamide, 1,3-hydroxyamide, 1,2-hydroxyoxime and 1,3-hydroxyoxime functionalities are also known to reversibly complex with phenylboronic acid under alkaline aqueous conditions similar to those associated with the retention of diol containing species (Tanner, D. W. and Bruice, T. C. (1967) *J. Amer. Chem. Soc.,* 89, 6954).

GENERAL METHODS FOR THE PREPARATION OF PHENYLBORONIC ACIDS

The most popular methods of synthesizing phenylboronic acids involve in situ generation of arylmagnesium or aryllithium species from aryl halides followed by transmetalation with a trialkoxyborate (Todd, M. H., Balasubramaniam, S. and Abell, C. (1997) *Tetrahedron Lett.,* 38, 6781–6784; Thompson, W. and Gaudino, J. (1984) *J. Org. Chem.,* 49, 5237–5243; Crisofoli, W. A. and Keay, B. A. (1991) *Tetrahedron Lett.,* 32, 5881–5884; Sharp, M. J., Cheng, W. and Sniekus, V. (1987) *Tetrahedron Lett.,* 28, 5093–5096; Larson, R. D., King, A. O., Cheng, C. Y., Corley, E. G., foster, B. S., Roberts, F. E., Yang, C., Lieberman, D. R., Reamer, R. A., Tschaen, D. M., Verhoeven, R. T. and Reider, P. J. (1994) *J. Org. Chem.,* 59 6391–6394).

Recently, transition-metal catalyzed cross coupling reactions have been developed to produce phenylboronic acids from aryl halides and alkoxydiboron (Ishiyama, T., Murata, M. and Miyaura, N. J. (1995) *Org. Chem.,* 60 7508–7510; Giroux, A., Han, Y. and Prasit, P. (1997) *Tetrahedran Lett.,* 38, 3841–3844) or dialkoxyhydroborane (Murata, M.; Watanabe, S.; Masuda, Y. *J. Org. Chem.* 1997, 62 6458–6459.) using $PdCl_2$ (dppf) as the catalyst.

Additionally, a palladium-catalyzed solid-phase boronation, using alkoxydiboron, has also been reported using a polymer-bound aryl halide (Piettre, S. R. and Baltzer, S. (1997) *Tetrahedron Lett.,* 38, 1197–1200).

PHENYLBORONATE BIOCONJUGATES

Ortho-substituted acetamidophenylboronic acids have been proposed as potential linkers for selective bioconjugation via the vicinal diol moieties of the carbohydrate residues associated with glycoproteins (Cai, S. X. and Keana, J. F. W. (1991) *Bioconjugate Chem.,* 2, 317–322).

Phenylboronic acid bioconjugates derived from 3-isothiocyanatophenylboronic acid have been successfully utilized for appending radioactive technetium dioxime complexes to monoclonal antibodies for use in medical imaging (Linder, K. E., Wen, M. D., Nowotnik, D. P., Malley, M. F., Gougoutas, J. Z., Nunn, A. D. and Eckelman, W. C. (1991) *Bioconjugate Chem.,* 2, 160–170; Linder, K. E., Wen, M. D., Nowotnik, D. P., Ramalingam, K., Sharkey, R. M., Yost, F., Narra, R. K. and Eckelman, W. C. (1991) *Bioconjugate Chem.,* 2, 407–414).

3-Aminophenylboronic acid has been covalently appended to proteins by a variety of chemical methods and the resulting phenylboronic acid bioconjugates tested for their binding of D-sorbitol, D-mannose and glycated hemoglobin (GHb). The interactions proved to be reversible and of very low affinity rendering the bioconjugates of very limited practical use. Similarly, an alkaline phosphatase phenylboronic acid bioconjugate used in an attempted enzyme-linked assay for the detection of GHb failed to detect the presence of glycated protein (Frantzen, F., Grimsrud, K., Heggli, D. and Sundrehagen, E. (1995) *Journal of Chromatography B,* 670, 37–45).

In addition to attempts to utilize immobilized phenylboronates for chromatographic separation of biological molecules having the requisite functionalities, a novel class of phenylboronic acid reagents and boronic compound complexing reagents have been developed for conjugating biologically active species (or bioactive species) and exploiting indirect bioconjugation through a reversible boron complex. These reagents and associated conjugates may be used in a manner analagous to Avidin-Biotin and Digoxigenin-anti-Digoxigenin systems. However, unlike the Avidin-Biotin and Digoxigenin-anti-Digoxigenin systems where the viability of the biological macromolecule must be maintained to preserve requisite binding properties, the bioconjugate formed through the boron complex is generally insensitive to significant variations in ionic strength, temperature, the presence of organic solvents, and the presence of chaotropic agents (protein denaturants). These phenylboronic acid reagents and boronic compound complexing reagents, their conjugates and bioconjugates as well as methods for their preparation and use are the subject of U.S. Pat No. 5,594,111, 5,623,055, 5,668,258, 5,648,470, 5,594, 151, 5,668,257, 5,688,928, 5,744,727, and 5,777,148.

Notwithstanding the substantial amount of research into bioconjugation, and the substantial amount of investment in this field, the selectivity of phenyldiboronic acid has not heretofore been successfully exploited to enable the conjugation of biological macromolecules with one another or with other molecular species that add useful properties.

SUMMARY OF THE INVENTION

The present invention relates to a novel class of phenyldiboronic acid (PDBA) reagents useful for the preparation of bioconjugates, and the method of making and using such reagents. In one embodiment, the PDBA reagents of the present invention are preferably complexed with boronic compound complexing reagents derived from salicylhydroxamic acid, or derivative thereof. In a second embodiment, the PDBA reagents of the present invention are preferably complexed with boronic compound complexing reagents derived from 2,6-dihydroxybenzohydroxamic acid, or derivatives thereof.

Unless otherwise noted, the phrase phenyldiboronic acid is used herein to include the broader class of diboronic compounds which complex with the boronic compound complexing reagents. In the present invention, in the place of prior art Avidin-Biotin and Digoxigenin anti-Digoxigenin systems, PDBA reagents are utilized in conjunction with boronic compound complexing reagents to facilitate chemical conjugation without the use of intermediary biological macromolecules. Bioconjugate preparation often involves the conjugation of several components including, but not limited to, proteins, peptides, polysaccharides, hormones, nucleic acids, liposomes and cells, with each other or with any other molecular species that add useful properties, including, but not limited to, drugs, radionuclides, toxins, haptens, inhibitors, fluorophores, ligands, and solid-phase supports including chromatographic supports. These various components utilized in bioconjugate preparation will collectively and individually be termed biologically active species or bioactive species.

Reagents suitable for the modification of a bioactive species for the purpose of incorporating one or more PDBA moieties for subsequent conjugation to a different (or the same) bioactive species having one or more pendant boronic compound complexing moieties are of the general formula of General Formula I,

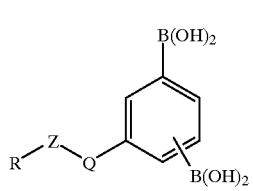

General Formula I wherein group R is a reactive electrophilic or nucleophilic moiety suitable for reaction of the PDBA reagent with a bioactive species. Group Z is a spacer selected from a saturated or unsaturated chain up to about 0 to 6 carbon equivalents in length, an unbranched saturated or unsaturated chain of from about 6 to 18 carbon equivalents in length with at least one intermediate amide or disulfide moiety, and a polyethylene glycol chain of from about 3 to 12 carbon equivalents in length. Group Q is a linkage that includes one of amide, either and thioether moieties.

Group R is preferably selected from, but not limited to, one of acrylamido, bromo, bromoacetamido, chloro, chloroacetamido, dithiopyridyl, hydrazide, N-hydroxysuccinimidyl ester, N-hydroxysulfo-succinimidyl ester, imidate ester, imidazolide, iodo, iodoacetamido, maleimido, amino and thiol moieties. Group Z is preferably an unbranched alkyl chain of the general formula $(CH_2)_n$, wherein n=1 to 6. Group Q is preferably selected from one of $NHCO$, $CONH$, $NHCOCH_2$, $CONHCH_2$, $O$, $OCH_2$, $S$ and $SCH_2$ moieties.

Reagents of General Formula I exhibit superior properties when compared to prior art phenylboronic acid reagents, in that, they incorporate two equivalents of boronic acid per reactive group R. Additionally reagents of General Formula I exhibit greater solubility than prior art phenylboronic acid reagents in aqueous buffers and polar solvents.

Reaction of a reagent of General Formula I with a bioactive species affords a conjugate having pendant PDBA moieties (one or more) of the general formula of General Formula II,

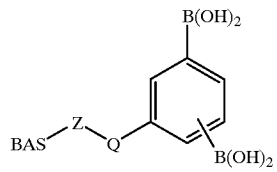

General Formula II wherein the symbol labeled BAS represents a biologically active species (or bioactive species) that may or may not contain a portion of a reactive moiety (which may itself have a spacer) used to attach the bioactive species to the reagent. It will be appreciated that, in many embodiments, several identical reagents of the general formula of General Formula I will react with a single BAS molecule. For example, if the BAS is a protein, many PDBA reagents will react with the protein, each reacting at one of the several sites on the protein which are reactive with the R group of the PDBA reagent. Group Z in General Formula II is a spacer selected from an aliphatic chain, such as a saturated or unsaturated chain up to about 0 to 6 carbon equivalents in length, an unbranched saturated or unsaturated aliphatic chain of from about 6 to 18 carbon equivalents in length with at least one intermediate amide and disulfide moieies, and a polyethylene glycol chain of from about 3 to 12 carbon equivalents in length. Group Q is a linkage that includes one of amide, ether and thioether moieties.

Conjugates of General Formula II exhibit reduced hydrophobic secondary properties as compared to phenylboronic acid conjugates known in the prior art. This reduction in hydrophobic secondary properties lowers the extent of non-specific binding, which is known to be a problem associated with bioactive species that have been conjugated with several hydrophobic moieties.

To form an indirect bioconjugate without the sue of an intermediary macromolecule the conjugate of General Formula II may be complexed with a boronic compound complexing conjugate. For example, boronic compound complexing reagents may be appended to a biologically active species to afford a conjugate having pendant boronic compound complexing moieties (one or more) of the general formula of General Formula III,

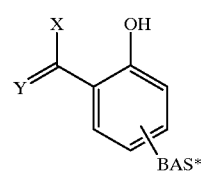

General Formula III wherein the symbol labeled BAS* represents a second bioactive species, that may include a linker portion and that may differ from the bioactive species labeled BAS. The BAS* may also include a portion of a reactive moiety used to attach the bioactive species to the boronic compound complexing reagent. In this example, group X is selected from one of $OH$, $NH_2$, $NHR'$, $NHOH$, and $NHOR'$, in which R' is selected from an alkyl (e.g., methyl, ethyl, etc.) and a methylene bearing an electronegative substituent, e.g., $CN$, $COOH$, etc. Group R' is preferably selected from one of $CH_3$, $CH_2CH_3$, $CH_2CN$, $CH_2COOH$, $CH_2CONH_2$ and $CH_2OCH_3$. Group Y is selected from one of $O$, $S$, and $NH$, and is preferably $O$.

Conjugates of the general formula of General Formula III, and methods for their preparation are the subject of U.S. Pat.

Nos. 5,594,151, 5,623,055, 5,648,470, 5,668,257, 5,668, 258, 5,688,928, 5,744,627, 5,847,192, 5,859,210, 5,869,623, and 5,852,178.

A conjugate of General Formula II, with at least one biologically active species and having pendent PDBA moieties (one or more), may be complexed with one or more conjugates of General Formula III, prepared from a second bioactive species BAS*, and having pendant boronic compound complexing moieties (one or more), to afford, for example, a bioconjugate of the general formula of General Formula IV,

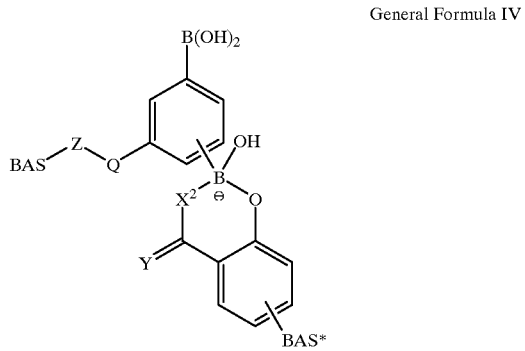

General Formula IV wherein the symbols labeled BAS and BAS*, and groups Z and Q are as were previously defined. Group $X^2$ is selected from one of O, NH, NR', NOH, and NOR', in which R' is selected from an alkyl (e.g., methyl, ethyl, etc.) and a methylene bearing an electronegative substituent, e.g., CN, COOH, etc. Group R' is preferably selected from one of $CH_3$, $CH_2CH_3$, $CH_2CN$, $CH_2COOH$, $CH_2CONH_2$ AND $CH_2OCH_3$. Group Y is selected from one of O, S, and NH, and is preferably O. In this manner, biological macromolecules may be conjugated to one another or with other functionalities that impart useful properties.

Alternatively, boronic compound complexing reagents may be appended to a biologically active species to afford a conjugate having pendant boronic compound complexing moieties (one or more) of the general formula of General Formula V,

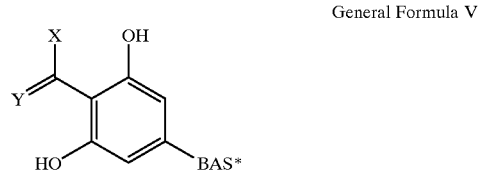

General Formula V wherein the symbol labeled BAS* represents a second bioactive species, that may include a linker portion and that may differ from the bioactive species labeled BAS. The BAS* may also include a portion of a reactive moiety used to attach the bioactive species to the boronic compound complexing reagent. Group X is selected from one of OH, OR, NH, NHR', NHOH, and NHOR', in which R' is selected from an alkyl (e.g., methyl, ethyl, etc.) and a methylene bearing an electronegative substituent, e.g., CN, COOH, etc. Group R' is preferably selected from on of $CH_3$, $CH_2CH_3$, $CH_2CN$, $CH_2COOH$, $CH_2CONH_2$ and $CH_2OCH_3$. Group Y is selected from one of O, S, and NH, and is preferably O.

Conjugates of General Formula V, and methods for their preparation are the subject of U.S. Pat. Nos. 5,777,148, 5,837,878, 5,777,148, and 5,872,224.

A conjugate of General Formula II, with at least one biologically active species and having pendent PDBA moieties (one or more), may be complexed with one or more conjugates of General Formula V, prepared form a second bioactive species BAS*, and having pendant boronic compound complexing moieties (one or more), to afford, for example, a bioconjugate of the general formula of General Formula VI,

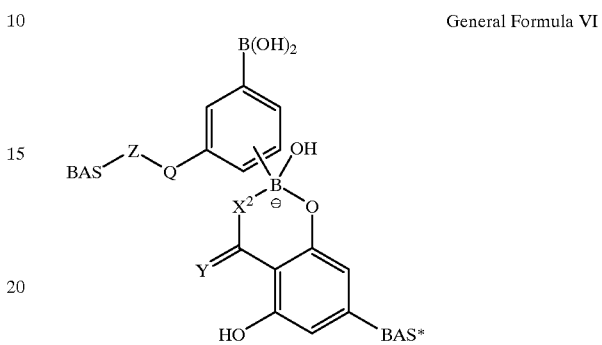

General Formula VI wherein the symbols labeled BAS and BAS*, and groups Z and Q are as were previously defined. Group $X^2$ is selected from one of O, NH, NR', NOH, and NOR', in which R' is selected from an alkyl (e.g., methyl, ethyl, etc.) and a methylene bearing an electronegative substituent, e.g., CN, COOH, etc. Group R' is preferably selected from one of $CH_3$, $CH_2CH_3$, $CH_2CN$, $CH_2COOH$, $CH_2CONH_2$ and $CH_2OCH_3$. Group Y is selected from one of O, S, and NH, and is preferably O. In this manner, biological macromolecules may be conjugated to one another or with other functionalities that impart useful properties.

Bioconjugates of General Formulas IV and VI may be prepared in buffered aqueous solution or organic solvents. The bioconjugate is formed within a few minutes over a range of temperatures of from about 4° C. to 70° C. The stability of the bioconjugate in aqueous solution at a given pH and temperature is significantly influenced by groups $X^2$ and Y. For example, bioconjugates of General Formula IV, wherein X is NOH and Y is O, are stable in aqueous solutions of approximate pH greater than 4.5 and less than 12.5. Bioconjugates of General Formula VI, wherein X is NOH and Y is O, are stable in aqueous solutions of approximate pH greater than 2.5 and less than 12.5. Consequently, bioconjugates of General Formula VI are preferred when working in buffered aqueous solutions at low pH.

The bioconjugation reaction (boronic acid complexation) is insensitive to significant variations in ionic strength, the presence of organic solvents, the presence of detergents, and the presence of chaotropic agents (protein denaturants), which are incompatible with prior art indirect labeling systems wherein the structure of a biological macromolecule must be maintained to preserve requisite binding properties. In most instances, the constraints governing the formation of bioconjugates, by the system herein described, are limited to those imposed by the conditions required to maintain viability (native conformation) of the bioactive species.

DETAILED DESCRIPTION OF THE INVENTION

Figure 1:
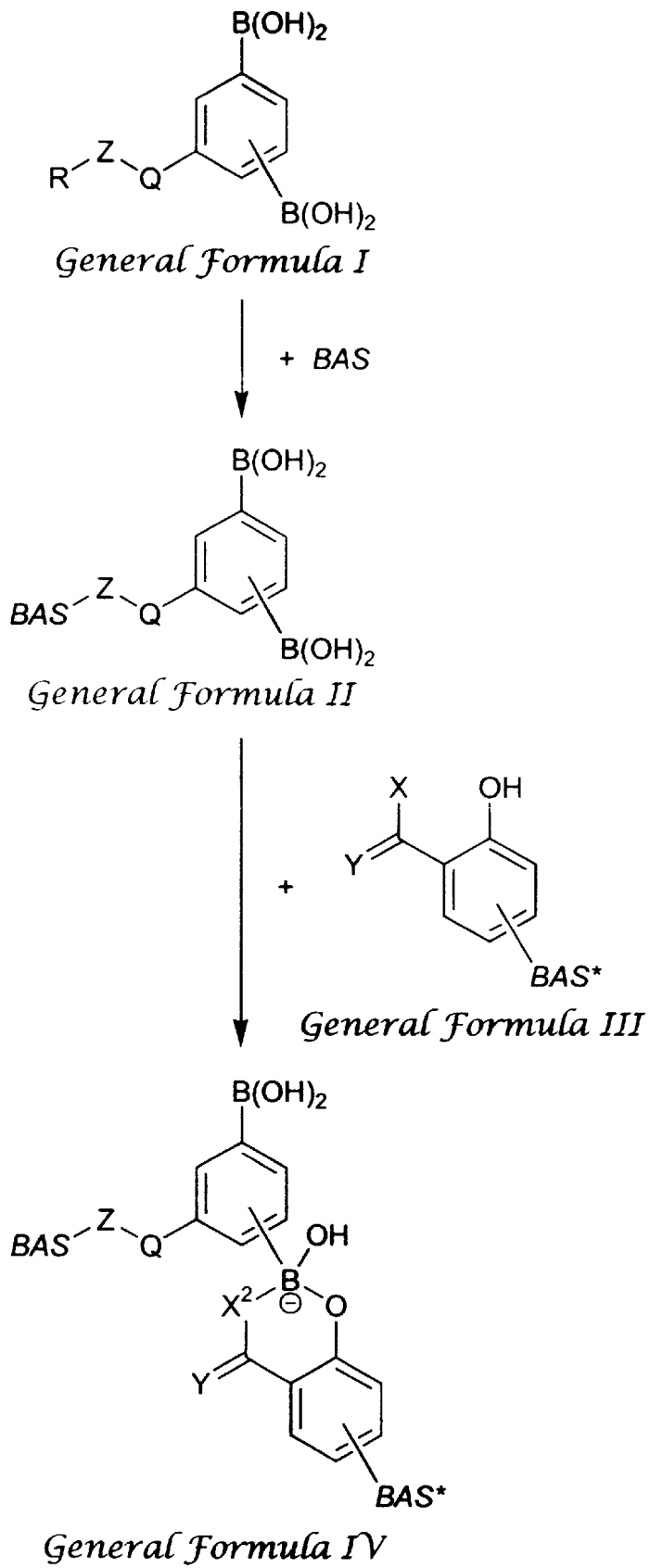
FIG. 1 illustrates the utilization of PDBA reagents of General Formula I to prepare conjugates of General Formula II. Conjugates of General Formula II may be utilized, in turn, in conjunction with boronic compound complexing conjugates of General Formula III, to prepare bioconjugates of General Formula IV.

The process which utilizes PDBA reagents of General Formula I for the preparation of bioconjugates is summarized in FIG. 1. Initially, a PDBA reagent of General Formula I is selected that is comprised of an appropriate reactive electrophilic or nucleophilic group R, suitable for reaction with a desired biologically active species (or bioactive species).

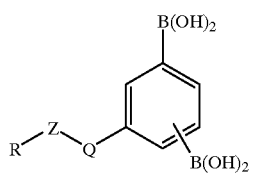

General Formula I

Group R is a reactive electrophilic or nucleophilic moiety suitable for reaction of the PDBA reagent with a bioactive species. Group R is preferably selected from, but not limited to, acrylamido, bromo, bromoacetamido, chloro, chloroacetamido, dithiopyridyl, hydrazide, N-hydroxysuccinimidyl ester, N-hydroxysulfosuccinimidyl ester, imidate ester, imidazolide, iodo, iodoacetamido, maleimide, amino and thiol moieties.

Group Z is a spacer selected from a saturated or unsaturated chain up to about 0 to 6 carbon equivalents in length, an unbranched saturated or unsaturated chain of from about 6 to 18 carbon equivalents in length with at least one intermediate amide or disulfide moiety, and a polyethylene glycol chain of from about 3 to 12 carbon equivalents in length. Group Z is preferably an unbranched alkyl chain of general formula (CH$_2$)$_n$, wherein n=1 to 6.

The PDBA reagent of General Formula I is condensed with the bioactive species to yield a PDBA conjugate of General Formula II,

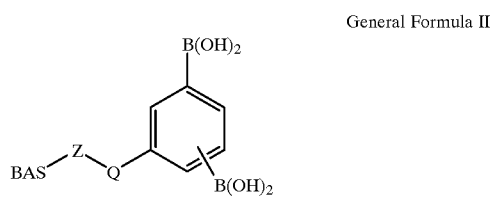

General Formula II wherein the symbol labeled BAS represents a biologically active species (or bioactive species) that may or may not contain a portion of a reactive moiety (which may itself have a spacer) used to attach the bioactive species to the reagent. It will be appreciated that, in many embodiments, several identical reagents of the general formula of General Formula I will react with a single BAS molecule. For example, if the BAS is a protein, many PDBA reagents will react with the protein, each reacting at one of the several sites on the protein which are reactive with the R group. Group Z in General Formula II is a spacer selected from a saturated or unsaturated chain up to about 0 to 6 carbon equivalents in length, an unbranched saturated or unsaturated chain of from about 6 to 18 carbon equivalents in length with at least one of intermediate amide or disulfide moieties, and a polyethylene glycol chain of from about 3 to 12 carbon equivalents in length. Group Q is a linkage that includes one of amide, ether and thioether moieties.

The PDBA conjugate of General Formula II is complexed with a boronic compound complexing conjugate. An example of a suitable boronic compound complexing conjugate is derived from salicylhydroxamic acid (SHA) and is of the general formula of General Formula III,

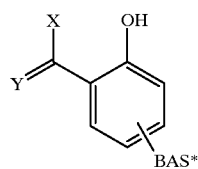

General Formula III wherein the symbol labeled BAS* represents a second biologically active species, that may include a linker portion and differ from the biologically active species labeled BAS of the complexing reagent. The BAS* may also include a portion of a reactive moiety used to attach the bioactive species to the boronic compound complexing reagent. The complexation yields the stereoisomeric complex (tetrahedral about the boron atom) of General Formula IV, General Formula IV

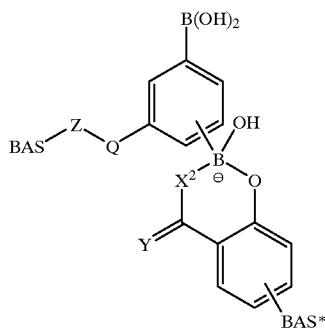

wherein the symbols labeled BAS and BAS*, and groups Z and Q are as were previously defined. Group $X^2$ is selected from one of O, NH, NR', NOH, and NOR', in which R' is selected from an alkyl (e.g., methyl, ethyl, etc.) and a methylene bearing an electronegative substituent, e.g., CN, COOH, etc. Group R' is preferably selected from one of $CH_3$, $CH_2CH_3CH_2CN$, $CH_2COOH$, $CH_2CONH_2$ and $CH_2OCH_3$. Group Y is selected from one of O, S, and NH, and is preferably O.

Figure 2:
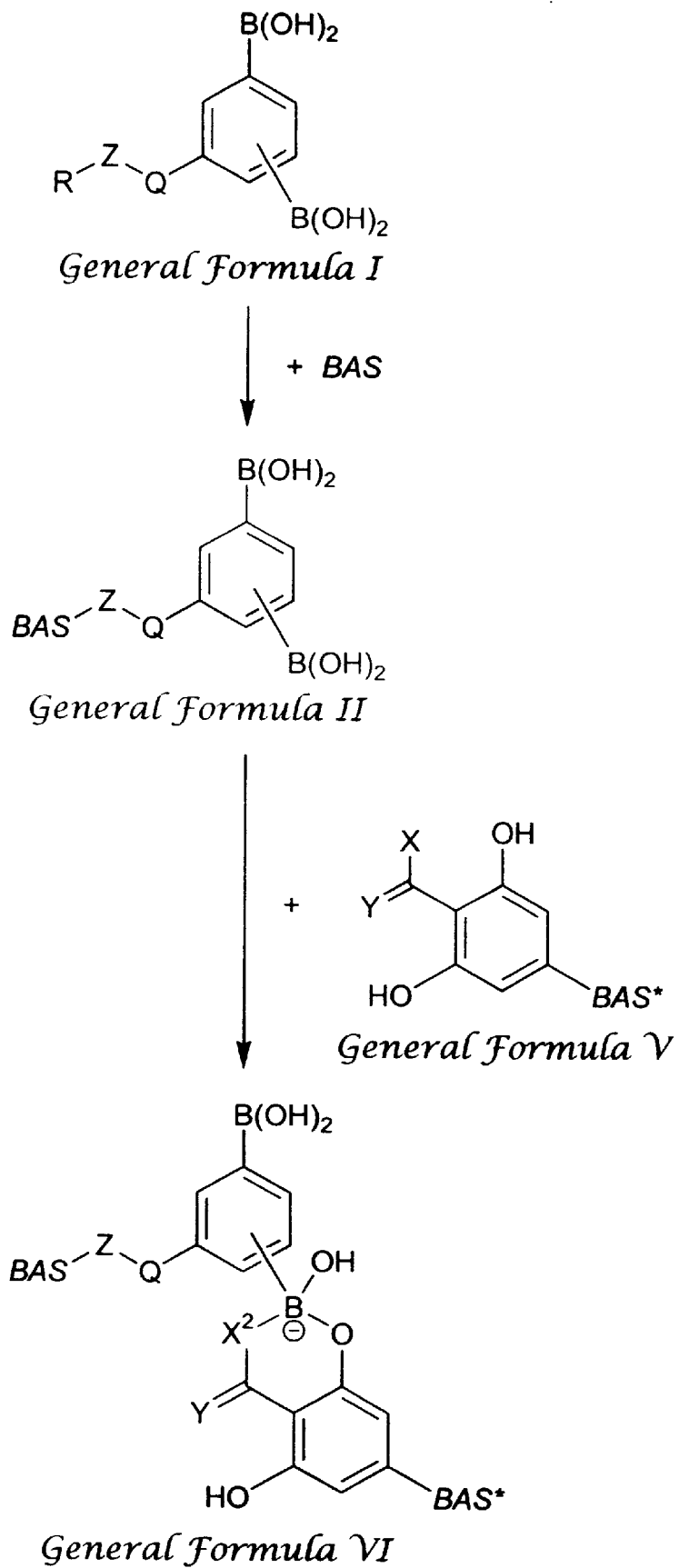
FIG. 2 illustrates the utilization of phenyldiboronic acid reagents of General Formula I to prepare conjugates of General formula II. Conjugates of General Formula II may be utilized, in turn, in conjunction with boronic compound complexing conjugates of General Formula V, to prepare bioconjugates of General Formula VI.

An alternative process which utilized PDBA reagents of General Formula I for the preparation of bioconjugates is summarized in FIG. 2. In this instance, the boronic compound complexing conjugates are derived from 2,6-dihydroxybenzohydroxamic acid (DHBHA). Thus, PDBA conjugates of General Formula II may be complexed with boronic compound complexing conjugates of General Formula V to afford bioconjugates of General Formula VI, General Formula VI

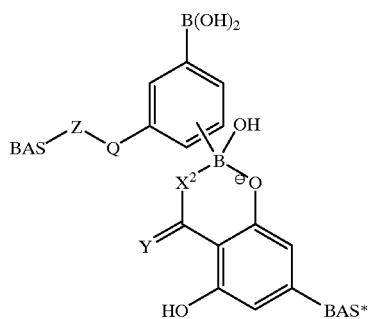

wherein the symbols labeled BAS and BAS*, and groups Z and Q are as previously defined. Group $X^2$ is selected from one of O, NH, NR', NOH, and NOR', in which R' is selected from an alkyl (e.g., methyl, ethyl, etc.) and a methylene bearing an electronegative substituent, e.g., CN, COOH, etc. Group R' is preferably selected from one of $CH_3$, $CH_2CH_3$, $CH_2CN$, $CH_2COOH$, $CH_2CONH_2$ and $CH_2OCH_3$. Croup Y is selected from one of O, S, and NH, and is preferably O.

BIOCONJUGATES COMPRISED OF TWO BORONIC COMPOUND COMPLEXING MOIETIES AND ONE PHENYLDIBORONIC ACID MOIETY

The presence of two phenylboronic acid moieties in PDBA conjugates of General Formula II enables the potential formation of bioconjugates derived from a phenylene-1,3-diboronic acid of the general formula of General Formula VII, General Formula VII

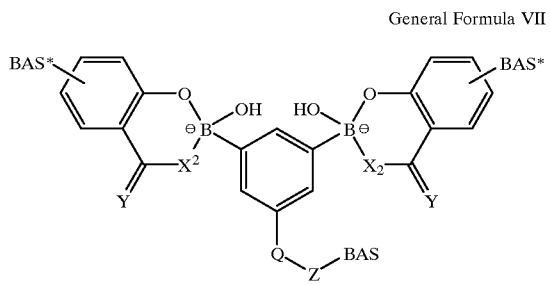

and conjugates derived from a phenylene-1,4-diboronic acid of the general formula of General Formula VII, General Formula VIII

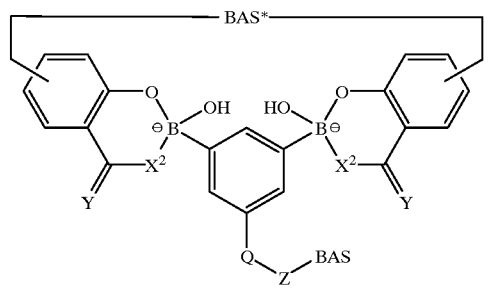

wherein the symbols labeled BAS and BAS*, and groups Z and Q are as were previously defined. Analogous structures involving one PDBA conjugate of General Formula II and two boronic compound complexing conjugates of General Formula V are also envisioned.

Alternatively, bioconjugates might result form complexation with a single bioactive species BAS* having adjacent boronic compound complexing moieties in close proximity to one another, to afford bioconjugates of the general formulas of General Formula IX and General Formula X, wherein a single bioactive species BAS* is shared by two boronic compound complexing moieties, General Formula IX General Formula X

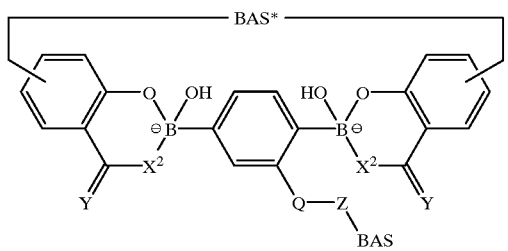

wherein the symbols labeled BAS and BAS*, and groups Z and Q are as were previously defined. This situation is often realized when the bioactive species is a densely modified surface. In this instance, PDBA conjugates of General Formula II bind with greater capacity and stability than do the various phenylboronic acid conjugates known in the prior art.

PREPARATION OF BIOCONJUGATES OF GENERAL FORMULAS IV, VI, VII, VIII, IX AND X

Bioconjugates of General Formulas IV, VI, VII, VIII IX and X may be prepared in buffered aqueous solutions or organic solvents. Preferred buffers include acetate, citrate, phosphate, carbonate and diglycine. Borate buffers should be avoided due to their ability to complex with the boronic compound complexing moiety. Tris, β-hydroxyamine and β-hydroxyacid buffers should be avoided due to their ability to complex with the phenyldiboronic acid. The bioconjugate is formed within a few minutes over a range of temperatures of from about 4° C. to 70° C. The stability of the bioconjugate in aqueous solution at a given pH and temperature is significantly influenced by groups $X^2$ and Y. For example, bioconjugates of General Formula IV, VII, VIII, IX and X, wherein X is NOH and Y is O, are stable in aqueous solutions of approximate pH greater than 4.5 and less than 12.5. Bioconjugates of General Formula VI, wherein X is NOH and Y is O, are stable in aqueous solution of approximate pH greater than 2.5 and less than 12.5. Consequently, bioconjugates of General Formula VI are preferred when working in buffered aqueous solutions at low pH. The stability of the phenylboronic acid complex toward acid catalyzed hydrolysis is related to the $pK_a$ of the hydroxamic acid participating in the complex. The lower the $pK_a$ of the hydroxamic acid moiety the more stable the complex.

The bioconjugation reaction (phenylboronic acid complexation) is insensitive to significant variations in ionic strength over the range 0.01 to 1 M; the presence of organic solvents including acetonitrile, methanol, ethanol, isopropanol, butanol, N,N-dimethylformamide and dimethylsulfoxide; the presence of detergents including SDS and Triton X100; and the presence of chaotropic agents (protein denaturants) including urea, guanidine hydrochloride, guanidine thiocyanate and formamide, which are incompatible with prior art indirect labeling systems wherein the structure of a biological macromolecule must be maintained to preserve requisite binding properties. Once formed, the bioconjugates are stable upon removal of water, and can be lyophilized for storage. In most instances, the constraints governing the formation of bioconjugates, by the system herein described, are limited to those imposed by the conditions required to maintain viability (native conformation) of the bioactive species.

PREPARATION OF REAGENTS OF GENERAL FORMULA I

The preparation of PDBA reagents of General Formula I are summarized in FIGS. 3–9. Preferred starting materials for the representative syntheses include 3,5-dibromobenzoic acid, 3,5-dibromotoluene, 2,5-dibromotoluene, 3,5-dibromophenol, 2,5-dibromophenol, and 1,4-dibromobenzene.

Figure 3:
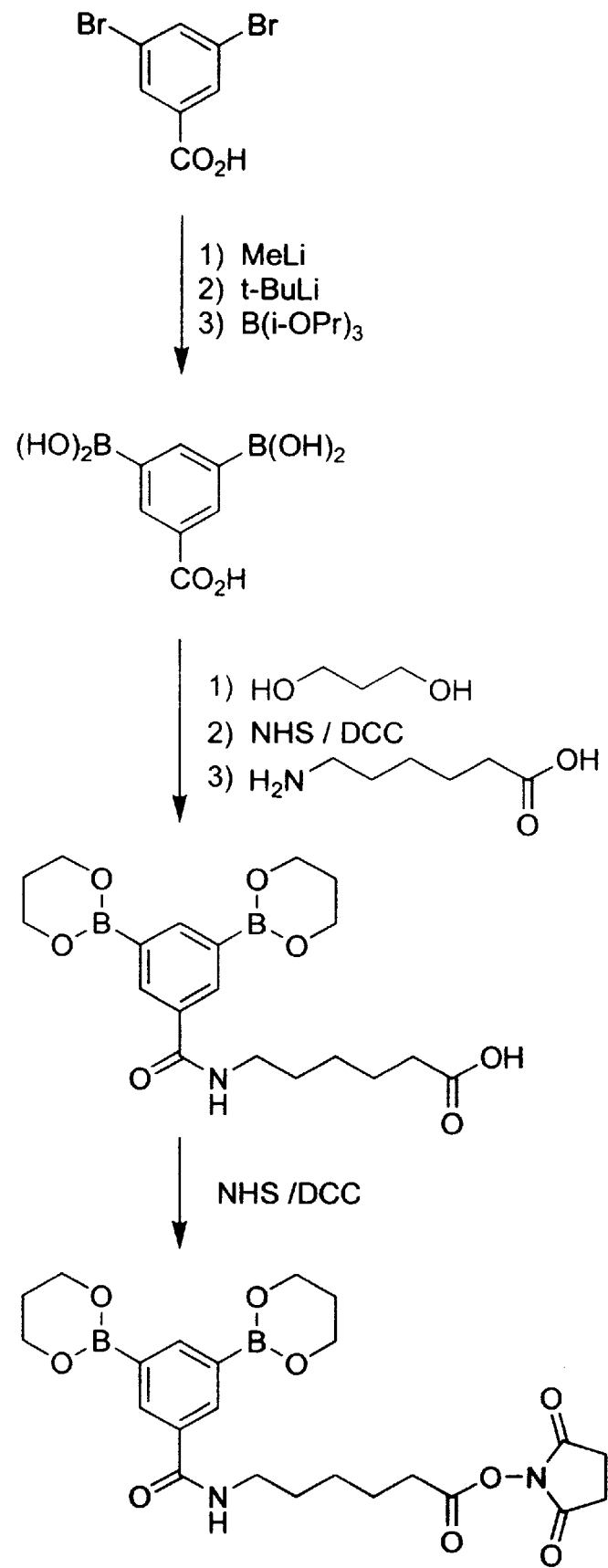
FIG. 3 summarizes the preparation of succinimidyl 1-carboxamidohexanoyl-3,5-diborylbenzene 1,3-propanediol diester, a preferred reagent of General Formula I.

FIG. 3 summarizes the preparation of succinimidyl 1-carboxamidohexanoyl-3,5-diborylbenzene 1,3-propanediol diester, a preferred reagent of General Formula I. The details of the synthesis of this reagent are disclosed in the examples that follow.

Figure 4:
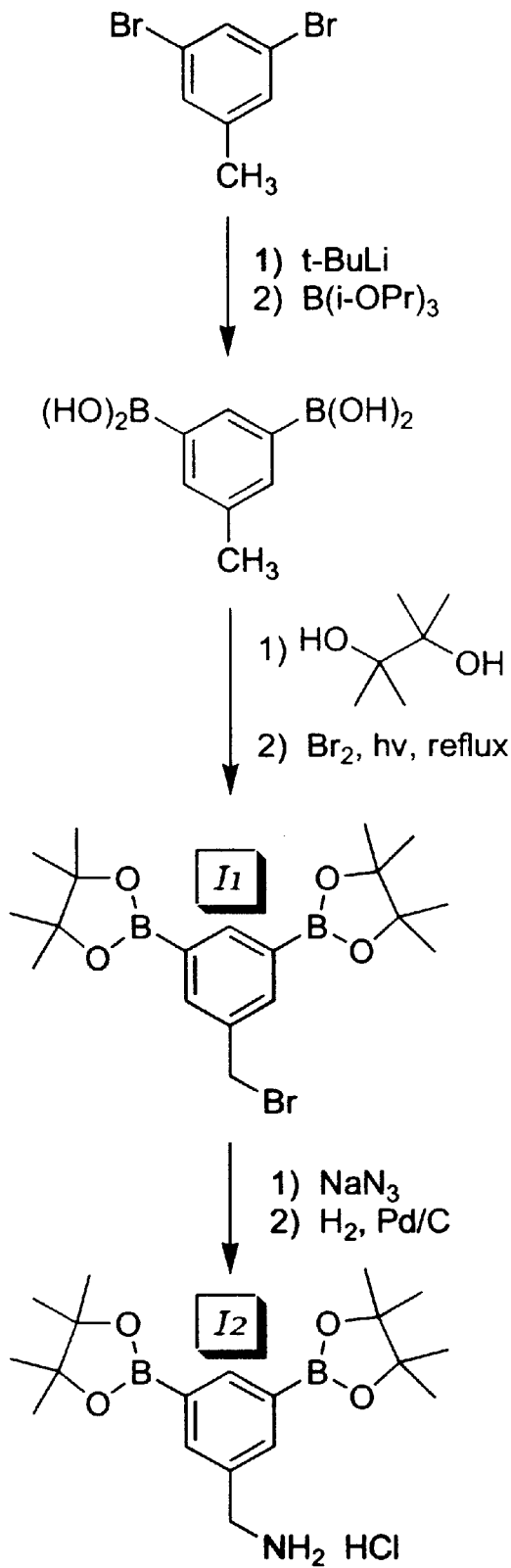
FIG. 4 summarizes the preparation of two synthetic intermediates, 1-bromomethyl-3,5-diborylbenzene pinacol diester (I1) and 1-aminomethyl-3,5-diborylbenzene pinacol diester (I2).

FIG. 4 summarizes the preparation of two synthetic intermediates, 1-bromomethyl-3,5-diborylbenzene pinacol diester (I1) and 1-aminomethyl-3,5-diborylbenzene pinacol diester (I2), which are prepared by boronation of 3,5-dibromotoluene with tert-butyl lithium and triisopropylborane (I1), and bromination of bis-3,5-[(dihydroxy)boryl] toluene (I2), respectively. The pinacol protecting groups associated with synthetic intermediates (I1) and (I2) are readily displaced upon dissolution of the synthetic intermediates into mildly acidic aqueous buffers such as acetate, and citrate buffers.

Figure 5:
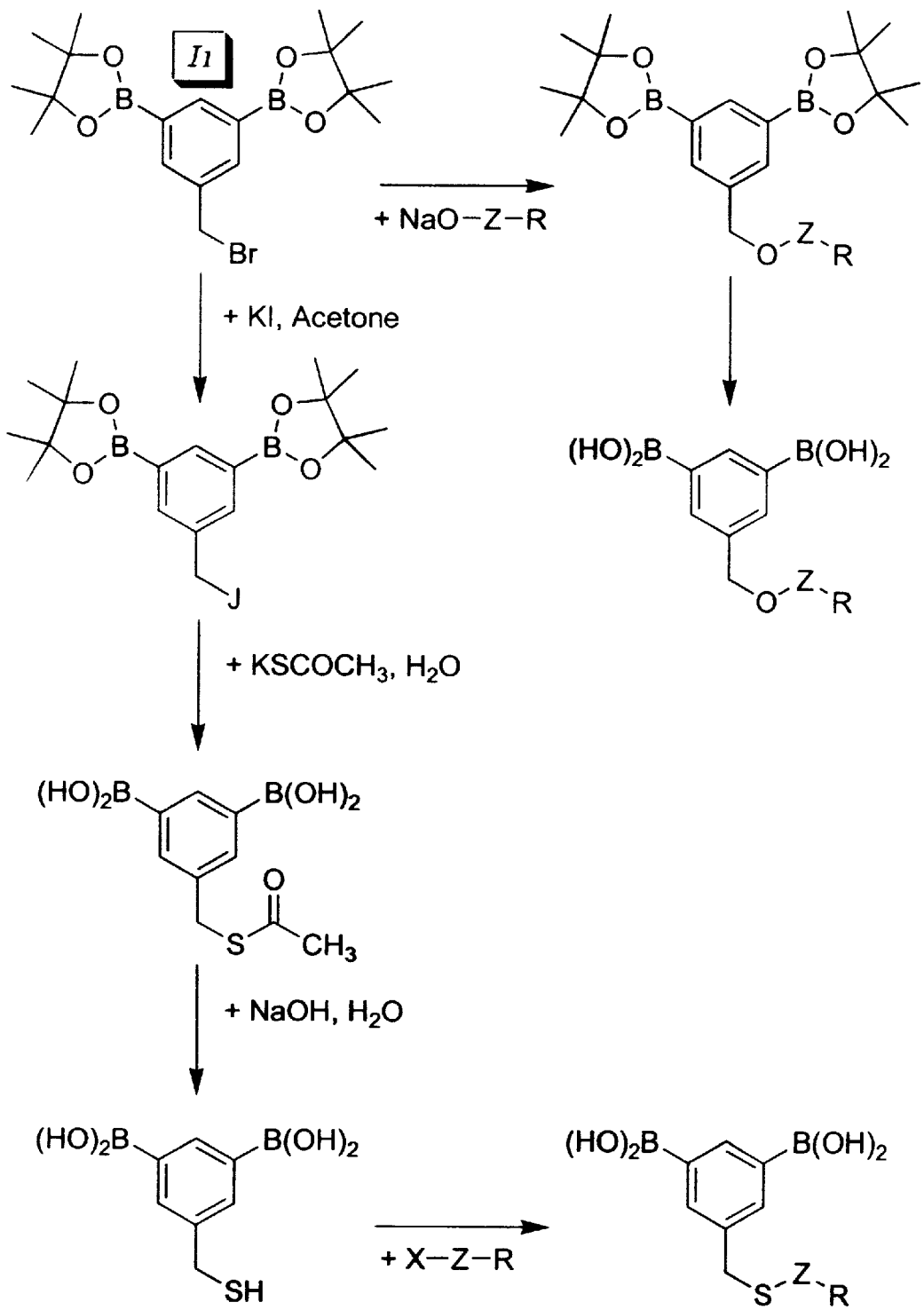
FIG. 5 summarized the preparation of reagents of General Formula I, derived from (I1), wherein the linkage Q is either an ether or thioether moiety.

FIG. 5 summarizes the preparation of reagents of General Formula I, wherein the linkage Q is comprised of wither an ether or thioether moiety. Synthetic intermediate (I1), 1-bromomethyl-3,5-diborylbenzene pinacol diester, may be alkylated with potassium thioacetate to afford S-acetyl-1-thiomethyl-3,5-diborylbenzene pinacol diester. Treatment of the thioester moiety with sodium hydroxide liberates the free thiolmethyl containing compound, which may be alkylated with alkyl halide of the general formula X—Z—R to afford reagents of General Formula I, wherein Q is a thioether moiety. Alternatively, reagents of General Formula I, wherein Q is an ether moiety, may be prepared by classic Williamson ether synthesis, in which, synthetic intermediate (I1), is alkylated with sodium slat of an aliphatic alcohol of the general formula NaO—Z—R as depicted in FIG. 5. Alternatively, reagents of General Formula I, wherein the linkage Q is comprised of either an aryl alkylether or aryl alkylthioether moiety, may be prepared from bis-3,5-[(dihydroxy)boryl]phenol and bis-3,5-[(dihydroxy)boryl] thiophenol, respectively.

Figure 6:
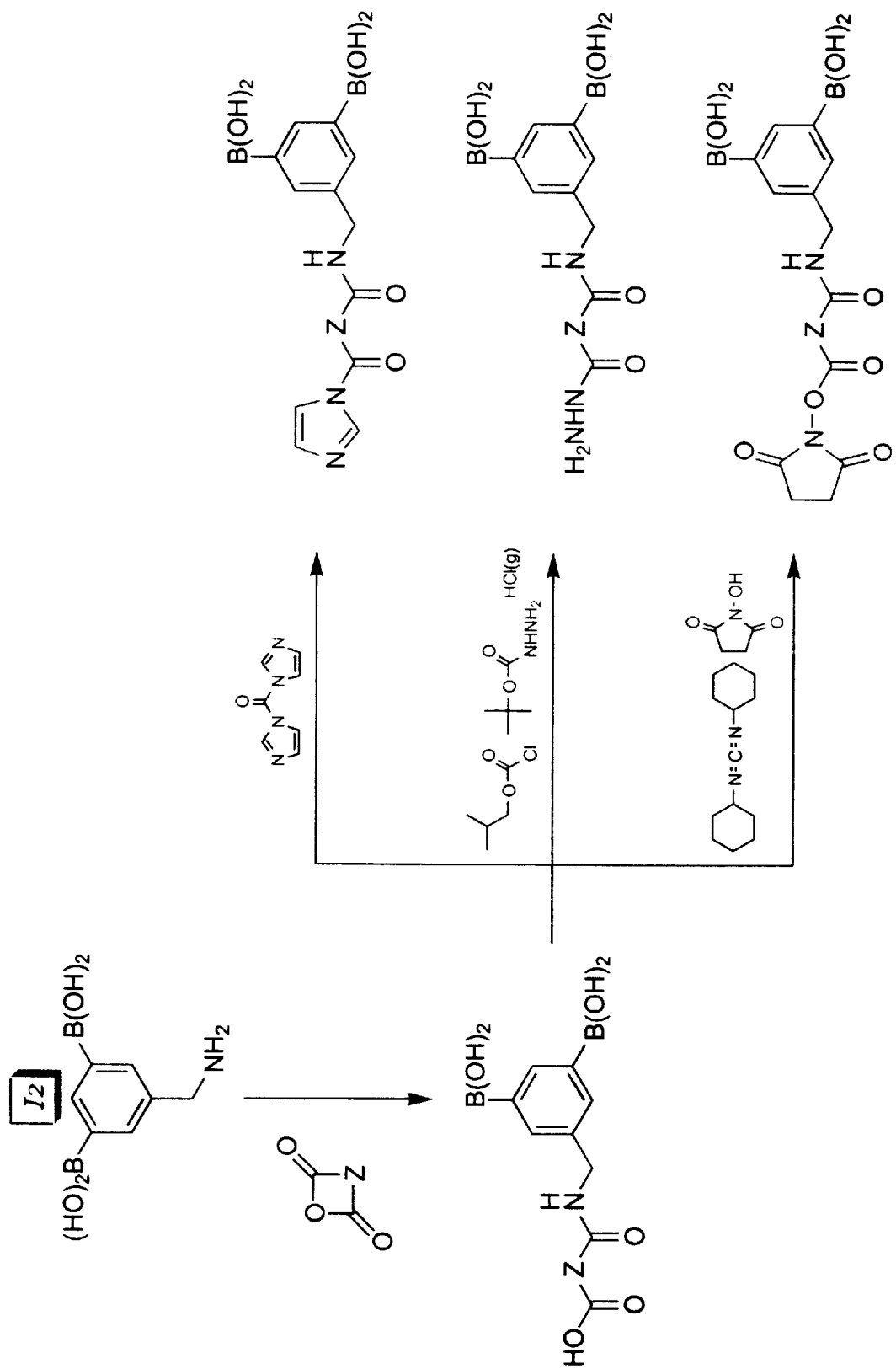
FIG. 6 summarizes the synthesis of reagents of General Formula I, derived from (I2), wherein Q is a CONHCH$_2$ moiety, and wherein R is selected from either imidazolide, hydrazide and N-hydroxysuccinimidyl ester moieties.

FIG. 6 summarizes the synthesis of reagents of General Formula I, wherein group R is selected from either imidazolide, hydrazide and N-hydroxysuccinimidyl ester moieties. These reagents are each prepared by a two-step process in which an aliphatic acid anhydride is utilized in the first step. Initially, 1-aminomethyl-bis-3,5-[(dihydroxy) boryl]benzene pinacol diester (I2), prepared as summarized in FIG. 4, is condensed of an aliphatic acid anhydride preferably selected from, but not limited to, either succinic anhydride, glutaric anhydride, and glycolic acid anhydride, in an aprotic organic solvent, which results in the introduction of a spacer (group Z) having a free terminal carboxylic acid moiety. Subsequently, the carboxylic acid moiety is further functionalized by reaction with either N,N-carbonyldiimidazole, isobutylchloroformate and tert-butyl carbazate, or N,N-dicyclohexylcarbodiimide and N-hydroxysuccinimide to afford the corresponding imidazolide, protected hydrazide and N-hydroxysuccinimidyl ester moiety, respectively. In the instance of the protected hydrazide, the N-(tert-butyloxycarbonyl) protecting group is removed by contacting the reagent with anhydrous hydrogen chloride.

Figure 7:
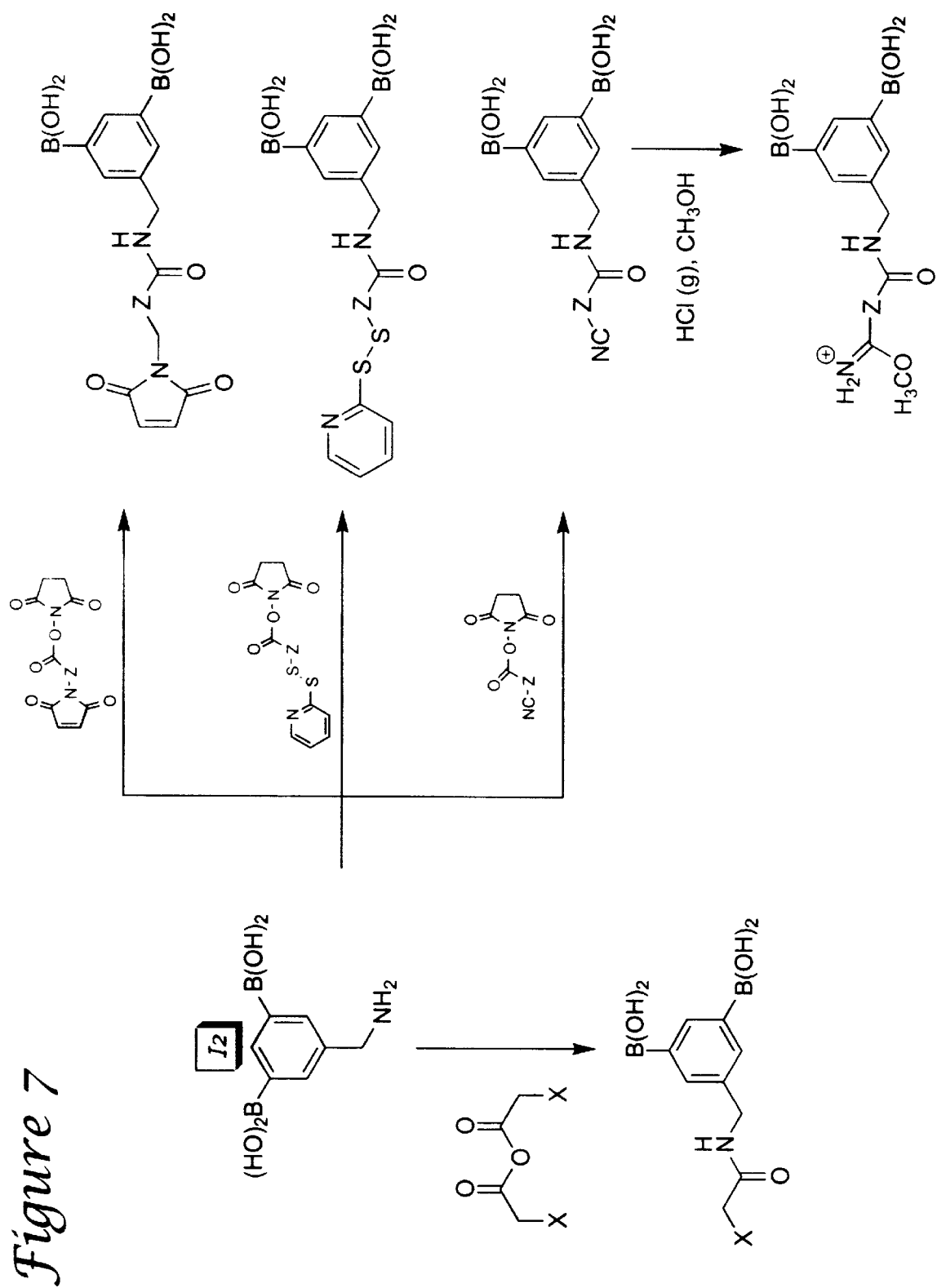
FIG. 7 summarizes the synthesis of reagents of General Formula I, derived from (I2), wherein Q is a CONHCH$_2$ moiety, and wherein R is selected from either bromo, chloro, iodo, maleimido, dithiopyridyl and imidate ester moieties.

FIG. 7 summarizes the synthesis of reagents of General Formula I, wherein group R is selected from either bromo, maleimido, dithiopyridyl and imidate ester moieties. Reagents of General Formula I, wherein group R is selected from either bromo and chloro moieties, are prepared by condensing 1-aminomethyl-bis-3,5-[(dihydroxy)boryl] benzene pinacol diester (I2), prepared as summarized in FIG. 4, with either bromoacetic acid anhydride or chloroacetic acid anhydride, respectively. The homologous iodo reagent is prepared by halogen exchange of the chloro reagent with sodium iodide. Reagents of General Formula I, wherein group R is selected from either maleimido and dithiopyridyl moieties, are prepared by condensing 1-aminomethyl-bis-3,5-[(dihydroxy)boryl]benzene pinacol diester (I2), prepared as summarized in FIG. 4, with an N-hydroxysuccinimidyl ester of an aliphatic carboxylic ester which bears either a terminal maleimido or dithiopyridyl moiety. Reagents of General Formula I, wherein R is an imidate ester moiety, are prepared by a two-step process in which 1-aminomethyl-bis-3,5-[(dihydroxy)boryl]benzene pinacol diester (I2), prepared as summarized in FIG. 4, is first condensed with an N-hydroxysuccinimidyl ester of an aliphatic carboxylic ester which bears a terminal nitrile moiety. Subsequently, the nitrile moiety is converted to the methyl imidate ester by reaction with anhydrous hydrogen chloride in methanol at 0° C.

Figure 8:
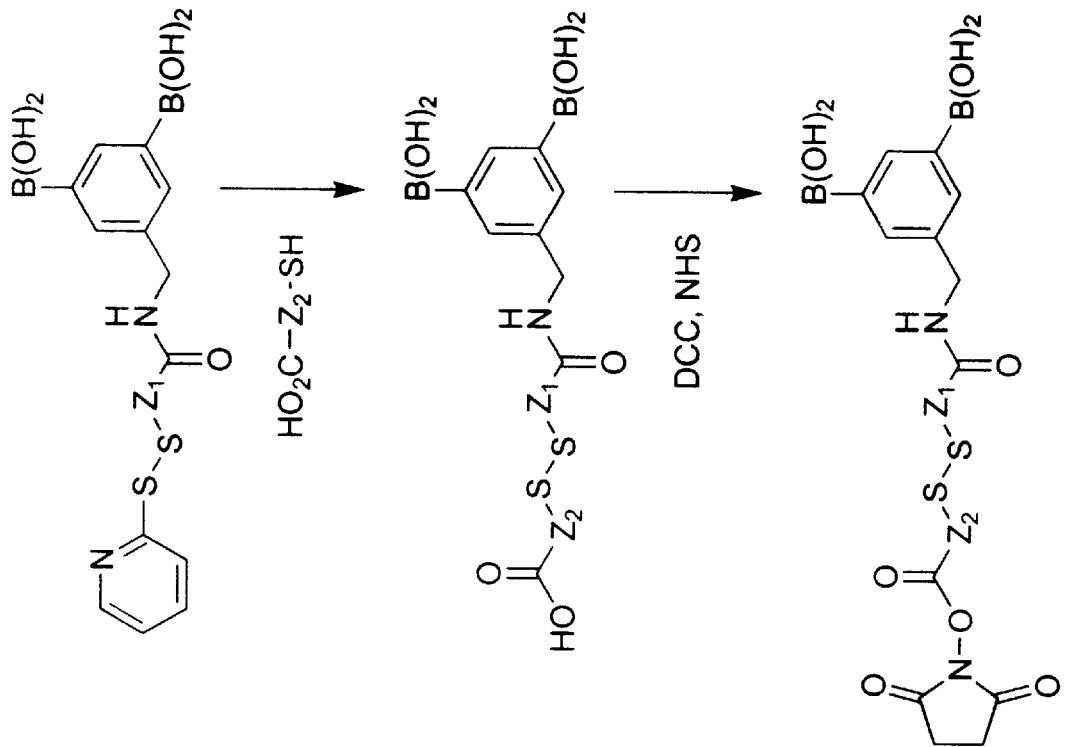
FIG. 8 summarizes the synthesis of reagents of General Formula I, derived from (I2), wherein Q is a CONHCH$_2$ moiety, and wherein R is an N-hydroxysuccinimidy ester moiety, and wherein Z is an unbranched saturated or unsaturated chain of from about 6 to 18 carbon equivalents in length with at least one of either an intermediate amide or disulfide moiety.
Figure 8:
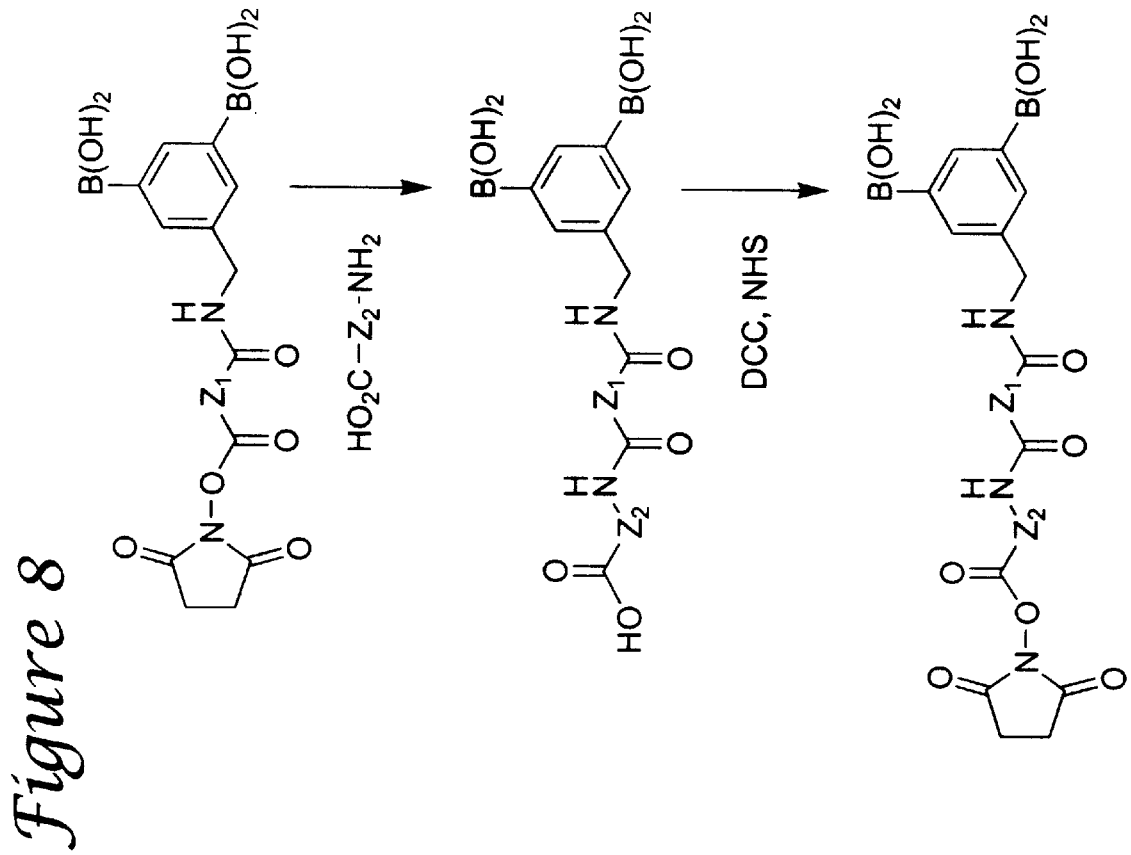

Reagents of General Formula I, wherein group R is selected from either N-hydroxysuccinimidyl ester and dithiopyridyl moieties may be utilized as synthetic intermediates to prepare reagents of General Formula I, wherein group Z is an unbranched saturated or unsaturated chain with at least one intermediate amide and disulfide moiety, as summarized in FIG. 8.

Reagents of General Formula I, wherein group R is an N-hydroxysuccinimidyl ester moiety prepared as summarized in FIG. 6, may be condensed with compounds having primary aliphatic amine moieties of the general formula $R-Z_2-NH_2$, wherein $Z_2$ is an unbranched saturated or unsaturated chain preferably of from about 1 to 5 carbon equivalents in length, to afford reagents of General Formula I, wherein group Z is an unbranched saturated or unsaturated chain with at least one intermediate amide moiety.

Alternatively, N-hydroxysuccinimidyl ester reagents of General Formula I, prepared as summarized in FIG. 6, and derived, for example, from a dicarboxylic acid anhydride preferably selected from, but not limited to, wither succinic anhydride, glutaric anhydride, and glycolic acid anhydride, may be condensed with compounds having primary aliphatic amine moieties of the general formula $HO_2C-Z_2NH_2$, wherein $Z_2$ is an unbranched saturated or unsaturated chain preferably of from about 1 to 5 carbon equivalents in length, preferably selected from, either glycine, β-alanine, amniopropiolic acid, 4-aminobutyric acid and 6-aminocaproic acid, to afford compounds having free terminal carboxylic acid moieties which may be further functionalized in accordance with FIG. 8 to afford reagents of General Formula 1, wherein Z is an unbranched saturated or unsaturated chain with at least one intermediate amide moiety.

Reagents of General Formula I, wherein group R is a dithiopyridyl moiety, prepared as summarized in FIG. 7, may be condensed with compounds having terminal thiol moieties of the general formula $R-Z_2-SH$, wherein $Z_2$ is an unbranched saturated or unsaturated chain preferably of from about 1 to 5 carbon equivalents in length, to afford reagents of General Formula I, wherein group Z is an unbranched saturated or unsaturated chain with at least one intermediate disulfide moiety.

Alternatively, dithiopyridyl reagents of General Formula I, prepared as summarized in FIG. 7, and, for example, derived from a mercaptocarboxylic acid selected from either mercaptoacetic acid, β-mercaptopropionic acid, mercaptopropiolic acid, 4-mercaptobutyric acid and 6-mercaptocaproic acid, may be condensed with compounds having a terminal thiol moiety of the general formula $HO_2C-Z_2-SH$, wherein $Z_2$ is an unbranched saturated or unsaturated chain preferably of from about 1 to 5 carbon equivalents in length, preferably selected from either mercaptoacetic acid, β-mercaptopropionic acid, mercaptopropiolic acid, 4-mercaptobutyric acid and 6-mercaptocaproic acid, to afford compounds having free terminal carboxylic acid moieties which may be further functionalized in accordance with FIG. 8 to afford reagents of General Formula I, wherein group Z is an unbranched saturated or unsaturated chain with at least one intermediate disulfide moiety.

Reagents of General Formula I, wherein group Z is a polyethylene glycol chain of from about 3 to 12 carbon equivalents in length, are prepared by 1-aminomethyl-3,5-diborylbenzene pinacol diester (I2), prepared as summarized in FIG. 4, with a polyethylene glycol reagent having both an N-hydroxysuccinimidyl ester moiety and either a reactive electrophilic or nucleophilic moiety (or a precursor thereof), many of which are commercially available, to afford reagents of General Formulal I, wherein group Z is a polyethylene glycol chain of from about 3 to 12 carbon equivalents in length.

Figure 9:
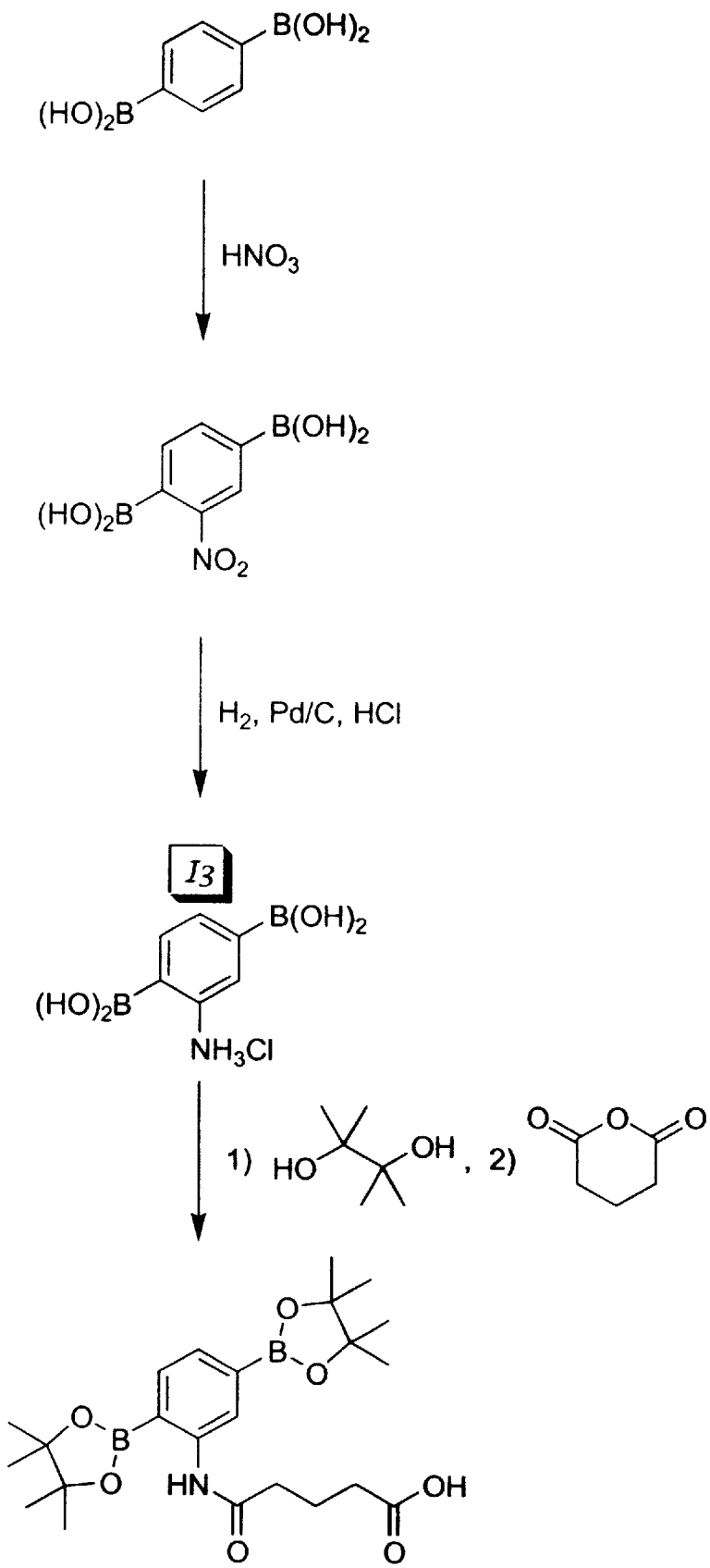
FIG. 9 summarizes the preparation of a synthetic intermediate, 1-amino-bis-2,5-[(dihydroxy)-boryl]benzene hydrochloride (I3).

FIG. 9 summarizes the preparation of a synthetic intermediate, 1-amino-bis-2,5-[(dihydroxy)boryl)benzene hydrochloride (I3), which is prepared by nitration of the commercially available phenylene-1,4-diboronic acid in the presence of hydrochloric acid. Synthetic intermediate (I3) may be employed to prepare reagents of General Formula I, wherein linkage Q is comprised of an amide moiety, in a manner analogous to that summarized in FIG. 6 and FIG. 7.

The following examples present a detailed description of the synthesis of reagents of General Formula I, the preparation of conjugates of General Formula II, and the preparation of bioconjugates of General Formulas IV and VI.

EXAMPLE I

Preparation of Bis-3,5-[(Dihydroxy)boryl]benzoic Acid

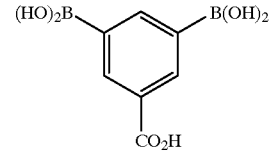

Dissolved 3,5-dibromobenzoic acid (5.00 g, 17.9 mmol) in tetrahydrofuran (300 mL) and cooled to −78° C. Added methyl lithium (1.4 M, 12.7 mL, 17.8 mmol) over 2 minutes, stirred for 5 minutes, and then added tert-butyl lithium (1.7 M, 58.0 mL, 98.6 mmol) over 5 minutes. Continued to stir at −78° C. for 15 minutes and then let warm to −45° C. Sitrred solution for 45 minutes and then cooled back to −78° C. Added triisopropylborane (27.0 mL, 117 mmol), stirred for 15 minutes, and then let warm to room temperature. After stirring at room temperature for 2 hours, removed solvents by rotary evaporation, and then removed the remaining organics under high vacuum while warming at 60° C. (1 h). Dissolved material in 60 mL of $H_2O$ and cooled to 0° C.

After one hour, filtered away solids (borate salts). Cooled filtrate to 0° C. and added concentrated HCl to pH of approximately 4. Let solution stand overnight at 4° C. Collected solids by filtration, washed with cold $H_2O$, and dried under high vacuum. Reduced volume of filtrate to 70 mL and let stand at 4° C. overnight. Collected solids by filtration, washed with cold $H_2O$, and dried under high vacuum. Obtained 2.23 g (60% yield, 0.770 g in 1st crop and 1.46 g in 2nd crop) of bis-3,5-[(dihydroxy)boryl]benzoic acid as a white powder.

$^1$H NMR (300 MHz, DMSO-d6) δ 8.18 (singlet, 4H, BOH), 8.41 (singlet, 3H, ArH), 12.65 (broad singlet, 1H, $CO_2H$). $^{13}$C NMR (75 MHz, DMSO-d6) δ 129.1, 133.5, 137.0, 144.9, 168.4. $^{11}$B NMR (121 MHz, DMSO-d6) δ 27.7.

EXAMPLE II

Preparation of Succinimidyl 1-Carboxamidohexanoyl-3,5-Diborylbenzene 1,3-Propanediol Diester

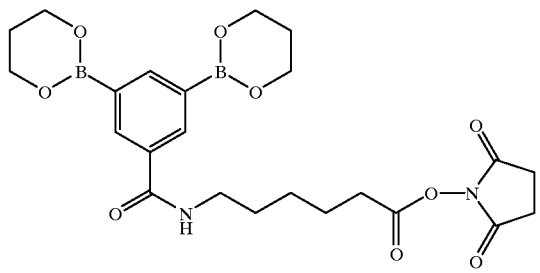

1-Carboxamidohexanoyl-3,5-Diborylbenzene

Suspended bis-3,5-[(dihydroxy)boryl]benzoic acid (3.191 g, 15.21 mmol) in dioxane (300 mL) and added 1,3-propanediol (2.20 mL, 30.4 mmol). Heated the solution to near reflux and stirred until solution became homogeneous. Removed solvent in vacuo. Redissolved (with heating) the material in 150 mL of dioxane and then again removed solvent in vacuo. Repeated once more. Dissolved material in 400 mL of dioxane with heating. Let solution cool to room temperature and added N-hydroxysuccinimide (1.84 g, 16.0 mmol) and dicyclohexylcarbodiimide (3.30 g, 16.0 mmol). Let stir overnight. Filtered away solids (dicyclohexylurea). Removed dioxane in vacuo and dissolved material in methanol (100 mL). Added 6-aminohexanoic acid (3.99 g, 30.4 mmol) and diisopropylethylamine (10.6 mL, 60.9 mmol). Stirred at room temperature for 24 hours. Removed solvent in vacuo, and took up material in 0.25 N NaOH (75 mL). Filtered away solids (dicyclohexylurea). Cooled solution to 0° C. and acidified with 1 N HCl to pH of approximately 4. Cooled at 4° C. for one day and then collected solids by filtration. Washed with cold $H_2O$ and dried under high vacuum. Obtained 3.59 g (73% yield) of 1-carboxamidohexanoyl-3,5-diborylbenzene.

$^1$H NMR (300 MHz, DMSO-d6) δ 1.29 (multiplet, 2H, $CH_2$), 1.51 (multiplet, 4H, $CH_2$), 2.19 (triplet, 2H, J=7.3 Hz, $CH_2CO_2H$), 3.22 (quartet, 2H, J=6.3 Hz, $CH_2NH$), 8.05 (broad singlet, 4H, BOH), 8.19 (singlet, 2H, ArH), 8.28 (singlet, 1H, ArH), 8.47 (triplet, 1H, J=11.1 Hz, NH), 11.92 (broad singlet, 1H, $CO_2H$). $^{13}$C NMR (75 MHz, MeOD) δ 24.0, 25.7, 28.3, 33.1, 39.0, 132.7, 133.3, 141.5, 169.5, 176.1 (carbonx attached to boron were too broad to observe).

Succinimidyl 1-Carboxamidohexanoyl-3,5-Diborylbenzene 1,3-Propanediol Diester

Suspended the 1-carboxamidohexanoyl-3,5-diborylbenzene (5.67 g, 17.6 mmol) in dioxane (200 mL) and added 1,3-propanediol (2.55 mL, 35.3 mmol). Heated to reflux and stirred for 15 minutes. Decanted solution into another flask and left behind any oily material. Removed dioxane in vacuo. Redissolved material in dioxane (150 mL) and removed once more. Repeated again. Finally, dissolved material in 200 mL of dioxane and added N-hydroxysuccinimide (2.18 g, 18.9 mmol) and dicyclohexylcarbodiimide (3.80 g, 18.4 mmol). Sitrred at room temperature overnight. Filtered away solids (dicyclohexylurea). removed solvent in vacuo. The material was then added to rapidly sitrred methyl t-butyl ether (250 mL) via a minimum amount of dioxane. The initial precipitate oils out. However, after stirring rapidly for 24 hours, a white solid is obtained. The solid is collected by filtration and washed with methyl tert-butyl ether. Obtained 6.52 g (74% yield) of succinimidyl 1-carboxamidohexanoyl-3,5-diborylbenzene 1,3-propanediol diester.

$^1$H NMR (300 MHz, DMSO-d6) δ 1.38 (multiplet, 2H, $CH_2$), 1.53 (multiplet, 2H, $CH_2$), 1.64 (multiplet, 2H, $CH_2$), 1.99 (pentent, 4H, J=5.1 Hz, $OCH_2CH_2CH_2O$), 2.66 (triplet, 2H, J=7.3 Hz, $CH_2CO_2$), 2.79 (singlet, 4H, $COCH_2CH_2CO$), 3.22 (quartet, 2H, J=6.4 Hz, $CH_2NH$), 4.10 (triplet, 8H, J=5.4 Hz, $OCH_2CH_2CH_2O$), 8.13 (singlet, 1H, ArH), 8.16 (singlet, 2H, ArH), 8.49 (triplet, 1H, J=5.5 Hz, NH). $^{13}$C NMR (75 MHz, DMSO-d6) δ 24.0, 25.4, 25.5, 26.9, 28.6, 30.1, 38.9, 61.6, 131.8, 133.4, 134.5, 141.6, 166.7, 169.2, 170.5.

EXAMPLE III

Preparation of 1-Bromomethyl-3,5-diborylbenzene Pinacol Diester

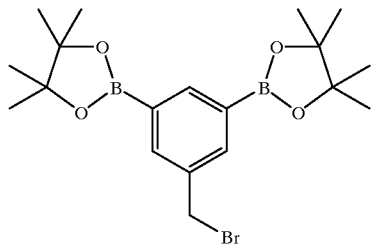

Bis-3,5-[Dihydroxy)boryl]toluene

Dissolved 3,5-dibromotoluene (5.27 g, 21.1 mmol) in tetrahydrofuran (300 mL) and cooled to −78° C. Slowly added tert-butyl lithium (1.7 M, 99.0 mL, 168 mmol) over 5 minutes and stirred at −78° C. for 10 min. Let solution warm to −45° C. and stirred for 1.5 hours. Cooled back to −78° C. and added triisopropylborane (49.0 mL, 212 mmol). After stirring for 10 minutes, the solution was allowed to warm to room termperature and stirred for 1.5 hours. Removed solvents by rotary evaporation. Removed the remaining organics under high vacuum while heating at 70° C. for 1 hour. Dissolved material in $H_20$ (100 mL). Cooled to 0° C. and let sit for 1 hour. Filtered away the solids (borate salts). Cooled filtrate to 0° C. and added conc. HCl to pH of approximately 3. Extracted with hexane (10 mL) the remove the oily material. Reduced the volume of $H_2O$, under vacuum, to 35 mL and let sit at 4° C. overnight. Collected solids by filtration, washed with cold $H_2O$, and dried under high vacuum. Obtained 1.94 g (53% yield) of 3,5-bis-[(dihydroxy)boryl]toluene.

$^1$H NMR (300 MHz, DMSO-d6) δ 2.27 (singlet, 3H, CH$_3$), 7.61 (singlet, 2H, ArH), 7.87 (singlet, 4H, B(OH), 7.98 (singlet, 1H, ArH). $^{13}$C NMr (75 MHz, DMSO-d6/D$_2$O) δ 21.1, 135.1, 136.7, 137.6, (carbons attached to boron were too broad to observe). $^{11}$B NMR (121 MHz, DMSO-d6/D2O) δ 28.5.

1-Bromomethyl-3,5-Diborylbenzene Pinacol Diester

Suspended bis-3,5-[(dihydroxy)boryl]toluene (1.22 g, 6.79 mmol) in dioxane (125 mL) and added pinacol (1.64 g, 13.9 mmol) and H$_2$O (15 mL). Heated to reflux, stirred until solution was homogenous, and then removed solvents in vacuo. Redissolved in 100 mL of dioxane, heated to reflux, and removed solvent in vacuo. Repeated once more. Dissolved material in carbon tetrachloride (125 mL). Heated to reflux and added a solution of bromine (385 uL, 7.47 mmol), in 20 mL of carbon tetrachloride, over 15 minutes while photolyzing with a white light (200 watt). Removed carbon tetrachloride in vacuo. Passed the material through a large plug of silica using methylene chloride as eluent. Collected the factions that came off with solvent front and contained UV active material. Removed methylene chloride in vacuo. Obtained pure 1-bromomethyl-3,5-diborylbenzene pinacol diester, 605 mg (21% yield) via repeated recrystallizations from hexane (3'20 mL).

$^1$H NMR (300 MHz, CDCl$_3$) δ 1.33 (singlet, 24H, CH$_3$), 4.51 (singlet, 2H, CH$_2$Br) 7.92 (singlet, 2H, ArH), 8.20 (singlet, 1H, ArH). $^{13}$C NMR (75 MHz, CDCl$_3$) δ 24.4, 33.0, 83.6, 136.2, 137.9, 141.0, (carbons attached to boron were too broad to observe). $^{11}$B NMR (121 MHz, CDCl$_3$) δ 30.4.

EXAMPLE IV

Preparation of 1-Aminomethyl-3,5-diborylbenzene Pinacol Diester Hydrochloride (I2)

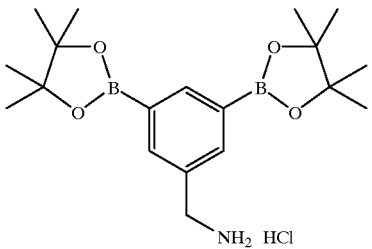

Dissolved 1-bromomethyl-3,5-diborylbenzene pinacol diester (II) (233 mg, 0.551 mmol) in 10 mL of dimethylformamide and added sodium azide (36.0 mg, 0.554 mmol). Stirred at room temperature overnight. Diluted with ethyl acetate (75 mL) and extracted with a 1:1 solution of saturated sodium chloride and 1 N HCl (10 mL×2). Dried with brine and over anhydrous magnesium sulfate. Removed solvents in vacuo and obtained the crude azide intermediate as a crystalline solid. Dissolved material in 20 mL of methanol. Added one drop of concentrated HCl and a small scoop of palladium on carbon (10%) catalyst. Stirred the solution under one atmosphere of hydrogen gas (balloon pressure) for 1.5 hours. Filtered away the catalyst and removed solvent in vacuo. Obtained 1-aminomethyl-3,5-diborylbenzene pincacol diester hydrochloride, 170 mg (78% yield) as a white crystalline solid.

$^1$H NMR (300 MHz, DMSO-d6) δ 1.29 (singlet, 24H, CH$_3$), 4.01 (singlet, 2H, CH$_2$HN$_3$), 7.89 (singlet, 2H, ArH), 8.01 (singlet, 1H, ArH),), 8.28 (broad singlet, 3H, CH$_2$NH$_3$). $^{13}$C NMR (75 MHz, DMSO-d6) δ 24.7, 66.4, 84.0, 128.3, 133.5, 138.3, 141.1.

EXAMPLE V

Preparation of 1-Carboxamidomethylhexanoyl-3,5-diborylbenzene Pinacol Diester

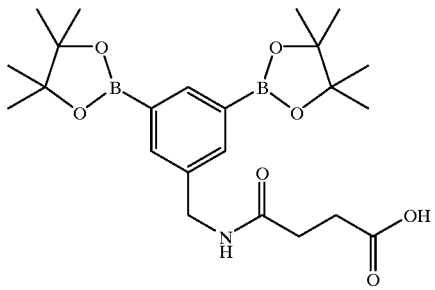

Dissolved 1-aminomethyl-3,5-diborylbenzene pincacol diester hydrochloride (I2) (150 mg, 0.379 mmol) in methylene chloride (10 mL) and added glutaric anhydride (52.0 mg, 0.456 mmol) and diisopropylethylamine (135 uL, 0.775 mmol). Stirred overnight at room temperature. Diluted with methylene chloride (60 mL) and extracted with a 1:1 solution of saturated sodium chloride and 1 N HCl (20 mL×2). Dried with brine and anhydrous magnesium sulfate. Chromatographed on silica gel using methylene chloride containing 4% methanol as eluent and collected the second set of fractions that stained positive with cerium-molybdate. Obtained 57.2 mg (32% yield) of desired product.

$^1$H NMR (300 MHz, CDCl$_3$) δ 1.31 (singlet, 24H, CH$_3$), 1.97 (pentet, 2H, J=7.0 Hz, CH$_2$CH$_2$CH$_2$), 2.30 (triplet, 2H, J=7.0 Hz, CH$_2$CH$_2$CH$_2$), 2.39 (triplet, 2H, J=7.0 Hz, CH$_2$CH$_2$CH$_2$), 4.43 (doublet, 2H, J=5.4 Hz, ArCH$_2$NH), 6.14 (triplet, 1H, J=5.4 Hz, NH), 7.78 (singlet, 2H, ArH), 8.16 (singlet, 1H, ArH).

EXAMPLE VI

Preparation of 1-Carboxamidohexanoyl-2,5-diborylbenzene Pinacol Dister

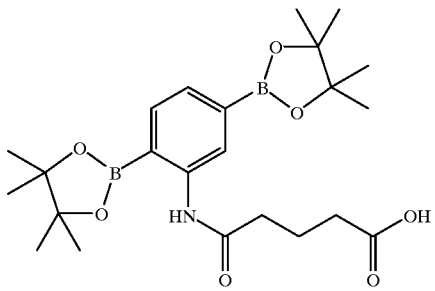

2-Nitro-bis-1,4-[(dihydroxy)boryl]benzene

To 15 mL of 90% nitric acid (d=1.49), cooled to ca. 0° C., a few crystals of urea was added, and the mixture was cooled to ca. −10° C. Powdered dry benzene 1,4-diboronic acid (5 g, 23.7 mmol) was added in small portions with rapid stirring over a period of 1 hour. After the addition, the mixture was stirred at −10° C. for 15 minutes, and then poured into a beaker with ice. The product was collected by filtration, washed with water and dried in vacuo. After recrystallization from water, 4.30 g (67% yield) of light yellow solid was obtained.

$^1$H NMR (300 MHz, DMSO-d$_6$) δ 7.48 (doublet, J=7.2 Hz, 1H), 8.06 (doublet, J=7.2 Hz, 1H), 8.49 (singlet, 1H).

$^{13}$C NMR (125 MHz, DMSO-d$_6$) δ 127.8, 131.8, 135.4, 137.2, 139.6, 149.9.

1-Amino-bis-2,5-[(dihydroxy)boryl]benzene Hydrochloride (I3)

A mixture of 2-nitro-bis-1,4-[(dihydroxy)boryl]benzene (0.50 g, 2.37 mmol) and 10% palladium on carbon (0.15 g) in methanol (10 mL) and concentrated HCl (0.2 mL) was stirred under hydrogen atmosphere for 1 hour. The catalyst was removed by filtration, and the filtrate was removed in vacuo to afford 0.49 g (95% yield)) of 1-amino-bis-2,5-[(dihydroxy)boryl]benzene hydrochloride as an off-white solid.

$^1$H NMR (300 MHz, DMSO-d$_6$) δ7.66 (singlet, 1H), 7.76 (doublet, J=7.2 Hz, 1H), 7.82 (doublet, J=7.2 Hz, 1H). $^{13}$C NMR (125 MHz, DMSO-d$_6$) δ 128.7, 133.2, 135.3, 135.4 (carbons attached to boron were too broad to observe).

1-Carboxamidohexanoyl-2,5-diborylbenzene Pinacol Diester

To a suspension of 1-amino-bis-2,5-[(dihydroxy)boryl]benzene hydrochloride (I3) (0.48 g, 2.2 mmol) in dry dioxane (60 mL) and methanol (2 mL), pinacol (0.52 g, 4.4 mmol) was added, and the mixture was heated to reflux, cooled to room temperature and evaporated in vacuo. The residue was again dissolved in dioxane, the solution evaporated in vacuo, and the residue dried in vacuo. The residue was dissolved in dry dichloromethane (15 mL), and the solution was treated with glutaric anhydride (0.25 g, 2.2 mmol), followed by diisopropylethylamine (0.28 g, 0.38 mL, 2.2 mmol). The reaction mixture was stirred at room temperature for 16 hours, diluted with dichloromethane (20 mL), and washed with 1M HCl (2×20 mL) and brine (20 mL). The organic layer was dried over anhydrous magnesium sulfate and filtered. A precipitate formed upon standing, which was colected by filtration and dried in vacuo to afford 0.27 g (27% yield) of an off-white solid.

$^1$H NMR (300 MHz, CDCl$_3$) δ 1.31 (singlet, 12H), 1.35 (singlet, 12H), 1.84 (multiplet, 2H), 2.22 (multiplet, 4H), 7.58 (doublet, J=7.2 Hz, 1H), 7.65 (doublet, J=7.2 Hz, 1H), 7.74 (singlet, 1H), 11.15 (br. singlet, 1H). $^{13}$C NMR (125 MHz, CDCl$_3$) δ 24.4, 25.2, 81.3, 83.6, 122.4, 131.8, 132.6, 137.8, 171.3, 175.3.

EXAMPLE VII

Preparation of Conjugates of General Formula II And Bioconjugates of General Formulas IV and VI Synthesis of 5'-PDBA-labeled Oligodeoxyribonucleotide Conjugates Oligodeoxyribonucleotide 7172 (sequence 5'-GATTACGCCAGTTGTACGGAC-3') was synthesized on a 1 μmole scale using standard automated phosphoramidite chemistry (Beckman Istruments Oligo 1000 and associated reagents). A protected amine-containing phosphoramidite (Aminolink 2, Applied Biosystems of UniLink Amino Modifier, Clontech) was employed on the same instrument to introduce one to four, reactive primary amines onto the 5'-end of the oligodeoxyribonucleotide using standard chemistry. The completed oligodeoxyribonucleotide was then cleaved from the support and the nucleobases deprotected using an UltraFast Deprotection kit (Beckman Instruments) and the protocol supplied by the manufacturer.

The amino-oligonucleotides were purified by ethanol precipitation, dissolved in 0.8 mL of 0.1 M NaHCO$_3$, and condensed with of succinimidyl 1-carboxamidohexanoyl-3,5-diborylbenzene 1,3-propanediol diester (PDBA-X-NHS) (5 mgs per mmole of primary amino groups on the amino-oligonucleotide in 0.2 mL of anhydrous N,N-dimethylformamide) for 2–18 hours at room temperature.

The crude PDBA-modified oligonucleotide was isolated from the reaction mixture by gel filtration on a KwikSep Dextran column (Pierce Chemical) in 0.1 M aqueous triethylammonium acetate, pH 6.5. The PDBA-modified oligonucleotide was then concentrated in a vacuum centrifuge to 1 mL, and purified by reverse phase HPLC on a 4.6 mm×250 mm C18 column, with a triethylammonium acetate-acetonitrile gradient. The desired product peak was collected and evaporated to a small pellet in a vacuum centrifuge, dissolved in 0.5 mL of water, and stored frozen.

Preparation of Salicylhydroxamic Acid (SHA) Magnetic Beads

Ten milliliters of unmodified M280 or M450 magnetic beads (Dynal) were gradually dehydrated into acetonitrile, and converted to aldehyde modified beads using oxalyl chloride activated N,N-dimethylsulfoxide and triethylamine in dichloromethane at −78° C. The resulting aldehyde bearing beads were gradually rehydrated and suspended in 5 mL of 0.1 M sodium acetate pH 5.5. The aldehyde groups were coupled with 4-glutarylaminomethylsalicylhydroxamic acid hydrazide (SHA-Z-NHNH$_2$) by adding 15–25 mgs dissolved in 200 uL N,N-dimethylsulfoxide, and rotating coupling reaction over night at room temperature. The beads were then washed extensively with water and stored in 5 mL of 10% ethanol.

Preparation of Salicylhydroxamic Acid (SHA) Sepharose 4B

SHA-Sepharose 4B was prepared by mixing 130 mg of (6-aminohexanoyl)-4-amino-methylsalicylhydroxamic acid (SHA-Z-NH$_2$), dissolved in 30 mL 0.2 M NaHCO$_3$, with. 6.5 g HCl washed CNBr activated Sepharose 4B (Pharmacia) overnight at room temperature. After the coupling reaction, 2 mL 0.5 M Tris, pH 8.5 were added and the gel slurry mixed at room temperature for 1 hour, and washed with water, 0.5 M NaCl, and water again. The resulting SHA-Sepharose 4B was suspended in 30 mL of 20% ethanol, and stored at 4° C.

Preparation of 2,6-Dihydroxybenzohydroxamic Acid (DHBHA) Sepharose 4B

DHBHA-Sepharose 4B was prepared by mixing 114 mg methyl (6-aminohexanoyl)-4-aminomethyl-2,6-dihydroxybenzoate [DHBA(OMe)-X-NH$_2$], dissolved in 30 mL 0.2 M NaHCO$_3$, with 5 g HCl washed CNBr activated Sepharose 4B (Pharmacia), overnight at room temperature. After the coupling reaction, the gel was washed with water and suspended in 50 ml. 0.1 M NH$_2$OH, pH 9, and rotated at room temperature for two hours. Finally, the gel was washed with water and suspended in 30 mL of 20% ethanol, and stored at 4° C.

Preparation of a Phenyldiboronic Acid-α-Biotin Antibody Conjugate

One milliliter of anti-Biotin monoclonal IgG$_1$ antibody (6.5 mg/mL in 0.1 M NaHCO$_3$) was conjugated with 440 nmoles of PDBA-X-NHS (7.4 ul of 60 mM PDBA-X-NHS dissolved in N,N-dimethylsulfoxide) for 1 hour at room temperature. Unconjugated PDBA-X-NHS and its hydrolysis products were removed by dialysis. The ultra-violet absorbance spectrum of the resulting conjugate (PDBA-anti-Biotin) exhibited an increase in A$_{260}$ relative to A$_{280}$ consistent with phenyldiboronic acid modification.

Preparation of a Phenyldiboronic Acid-Alkaline Phosphatase (PDBA-AP) Conjugate

One milliliter of alkaline phosphatase (Sigma, 6 mg/mL) was dialyzed against one liter of 0.1 M NaHCO$_3$, and conjugated with 700 nmoles of PDBA-X-NHS (10 uL of 70 mM stock in N,N-dimethylformamide) for two hours on ice. Unconjugated PDBA-X-NHS and its hydrolysis products were removed by dialysis in 0.1 M $NaHCO_3$. The ultraviolet absorbance spectrum of the resulting conjugate (PDBA-AP) exhibited an increase in $A_{260}$ relative to $A_{280}$ consistent with phenylboronic acid modification. The conjugate was stored at 4° C.

Preparation of a 2,6-Dihydroxybenzohydroxamic Acid-Alkaline Phosphatase Conjugate One milliliter of alkaline phosphatase (Sigma, 6 mg/mL) was dialyzed against one liter of 0.1 M $NaHCO_3$, and conjugated with 714 nmoles of methyl 4-glutarylaminomethyl-2,6-di-hydroxybenzoate succinimidyl ester [DHBA(OMe)-Z-NHS] (10.5 uL of 68 mM in N,N-dimethylformamide) for two hours on ice. The methyl ester of the conjugate was converted to a hydroxamic acid by adding one milliliter of 2 M $NH_2OH$, pH 10, and incubating the reaction at 4° C. for six days. The $NH_2OH$ reaction mixture was then dialyzed against 0.1 M $NaHCO_3$ and stored at 4° C.

Preparation of a Salicylhydroxamic Acid-Goat α-Mouse Antibody Conjugate

Two milliliters of goat α-mouse antibody (Rockland, 8.8 mg/mL in 0.1 M $NaHCO_3$) were conjugated with 2.35 umoles of methyl 4-glutarylaminomethylsalicylate succinimidyl ester [SA(OMe)-Z-NHS] for 1 hour at room temperature. The methyl ester of the conjugate ws converted to a hydroxamic acid by adding two milliliters of 2 M $NH_2OH$, pH 10, adjusting the pH to 10 with 1 N NaOH, and incubating the reaction at room temperature for three days. $NH_2OH$ and unconjugated SA(OMe)-X-NHS and its hydrolysis products were removed by gel filtration on a G-25 Sephadex column (Pharmacia) in 0.1 M $NaHCO_3$, and the conjugate (SHA-goat α-mouse) was stored at 4° C.

Preparation of a 2,6-Dihydroxybenzohydroxamic Acid-Goat α-Mouse Antibody

Two milliliters of goat α-mouse antibody (Rockland, 8.8 mg/mL in 0.1 M $NaHCO_3$) were conjugated with 2.35 umoles of with DHBA(OMe)-Z-NHS for 1 hour at room temperature. The methyl ester of the conjugate was converted to a hydroxamic acid by adding two milliliters of 2 M $NH_2OH$, pH 10, adjusting the pH to 10 with 1 N NaOH, and incubating the reaction at room temperature for three days. $NH_2OH$ and unconjugated DHBA(OMe)-X-NHS and its hydrolysis products were removed by gel filtration on a G-25 Sephadex column (Pharmacia) in 0.1 M $NaHCO_3$, and the conjugate (DHBHA-goat α-mouse) stored at 4° C.

Polymerase Chain Reaction (PCR) Protocol

A region of Lambda DNA (801bp) was amplified by the polymerase chain reaction. The PCR reaction contained 200 uM dATP, dCTP, dGTP, and dTTP in addition to Biotin- and PDBA-modified oligoncelotide primers at 1 uM in 1X PCR Buffer II (Perkin Elmer), Lambda DNA (1 ng/uL), and 1U of *Thermus aquaticus* DNA polymerase. The reaction mixture was denatured at 92° C. for one minute and amplified by 35 cycles of PCR at 95° C. for 10 seconds, 62° C. for 20 seconds, and 72° C. for 30 seconds, with a final extension at 72° C. for 5 minutes. The reaction produced 50–100 ng of amplified product (801 bp), which exhibited retarded mobility relative to unmodified PCR product during electrophoresis on 1% agarose gels in 50 mM Tris, 100 mM borate, 2 mM EDTA, pH 8.3.

EXAMPLE VIII

Preparation of Bioconjugates of General Formula VI Sandwich Hybridization Detection of Nucleic Acid Probes on Magnetic Particles A 42-mer oligonucleotide was hybridized with two 21-mer oligonucleotides bearing 5'-PDBA and Biotin labels in 1.5 M NaCl, 150 mM sodium citrate, pH 7, at 45° C. for ten minutes. Twenty-five microliters of the hybridization mixture was mixed with twentyfive microliters of M280 streptavidin-magnetic particles (Dynal) in a polypropylene microwell plate well. After 30 minutes, the magnetic particles were captured in the bottom of the well with a magnetic plate, and washed five times with 150 mM NaCl, 20 mM Tris-HCl, 0.02% Tween 20, pH 8.

One hundred microliters of DHBHA-AP (1 ug/mL in 1 mg/mL BSA, 140 mM NaCl, 10 mM Tris-HCl, pH 8) were added to the magnetic particles and mixed well. After 30 minutes, the magnetic particles were captured in the bottom of the well with a magnetic plate, and washed six times with 150 mM NaCl, 20 mM Tris-HCl, 0.02% Tween20, pH 8. Alkaline phosphatse substrate (1 mg/mL p-nitrophenylphosphate in 1 M diethanolamine buffer, 1 mM $MgCl_2$, 0.1 mM $ZnCl_2$, pH 10.4) was added, and incubated at 37° C. for 90 minutes. The Absorbance at 405 nm ($A_{405}$) was measured with an ELISA plate reader (Molecular Devices).

A strong $A_{405}$ was produced when all components of the hybridization sandwich were present, and the signal was proportional to the amount of 42-mer present. Experimental controls lacking either the 42-mer, the Biotin-oligonucleotides and PDBA-oligonucleotides did not produce a significant $A_{405}$.

EXAMPLE IX

Preparation of Bioconjugates of General Formula VI Sandwich Hybridization Detection of Nucleic Acid Probes in Multiwell Plates Detection of PDBA-Labeled PCR Product on DHBHA-Coated Microwell Plates The wells of a polystyrene microwell plate (Becton Dickinson) were coated with DHBHA by filling the wells with 200 uL of DHBHA-goat α-mouse conjugate (30 ug/mL in 0.1 M $NaHCO_3$ pH 9.0) and incubating overnight at 4° C. The coating solution was removed and the plate backcoated with 5 mg/mL BSA (300 ul per well in 0.2 M $NaHCO_3$, pH 9.0) for 1 hour at room temperature. The BSA solution was removed by washing the plate five times with ELISA Wash Buffer (150 mM NaCl, 20 mM Tris-HCl, 0.02% Tween 20, pH 8.0).

One hundred microliters of unpurified PDBA and biotin labeled PCR product were added to 900 ul of 1.5N NaCl, 150 mM sodium citrate, pH 7.0 (10× SSC) and serially-diluted in 10× SSC. One hundred microliters of the diluted PCR products were added to the wells and incubated for one hour at room temperature. The plate was then washed five times with ELISA Wash Buffer, and 100 ul of Streptavidin-Alkaline Phosphatase (Boehringer Mannheim, 0.2 U/mL in 1 mg/ml BSA, 140 mM NaCl, 10 mM Tris-HCl, pH 8.0) were added to each well and incubated for thirty minutes at room temperature.

The plate was washed 5 times with ELISA Wash Buffer, and 200 ul of p-nitrophenylphosphate (1 mg/mL in diethanolamine, 1 mM $MgCl_2$, 0.1 mM $ZnCl_2$, pH 10.4) were added to the plate and incubated at 37° C. for 30–60 minutes. Less than 1 uL of PCR product was detected. PCR product lacking either PDBA or biotin labels was not detected.

EXAMPLE X

Preparation of Bioconjugates of General Formula IV Detection of PDBA-Labeled PCR Product Detection of PDBA- & Biotin-Labeled PCR Product on SHA-Magnetic Beads PDBA- and biotin-labeled PCR product (0.02 μL of 1.5 M NaCl, 150 mM sodium citrate, pH 7 (10× SSC), and added to a polypropylene microwell plate well containing SHA-magnetic particles (10–50 ul). The particles and PCR product were mixed occasionally for 30–60 minutes at room temperature. The magnetic particles were captured in the bottom of the wells with a magnetic plate and washed five times in 150 mM NaCl, 20 mM Tris-HCl, 0.02% Tween 20, pH 8 (ELISA Wash Buffer). One hundred microliters of streptavidin alkaline-phosphatase (Boehringher Mannheim, 0.2 U/mL in 1 mg/mL BSA, NaCl, Tris-HCl, pH 8) were added and mixed with the magnetic particles for 30 minutes at room temperature. The magnetic particles were captured in the bottom of the wells with a magnetic plate and washed 5 times with ELISA Wash. Alkaline phosphatase substrate was added (1 mg/ml p-nitrophenyl phosphate in 1M diethanolamine buffer, 1 mM $MgCl_2$, 0.1 mM $ZnCl_2$, pH 10.4), and the color developed at 37° C. for 10–60 minutes. The lower limit of detection was 50 pg of PCR product.

EXAMPLE XI

Preparation of Bioconjugates of General Formula IV Detection of a PDBA-Labeled Oligonucleotide Hybrid Detection of a PDBA-Labeled Oligonucleotide Hybridized to a Biotin-Labeled Oligonucleotide A 42-mer oligonucleotide was hybridized with two 21-mer oligonucleotides bearing 5'-PDBA and Biotin labels in 1.5 M NaCl, 150 mM sodium citrate, pH 7, at 45 C. for ten minutes. Twenty-five microliters of the hybridization mixture was mixed with 1–50 uL of SHA-magnetic particles (Dynal, M450) in a polypropylene microwell plate well. After 30 minutes, the magnetic particles were captured in the bottom of the well with a magnetic plate, and washed five times with 150 mM NaCl, 20 mM Tris-HCl, 0.02% Tween 20, pH 8.

One hundred microliters of streptavidin-alkalive phosphatase conjugate (SA-AP) (1 ug/mL in 1 mg/mL BSA, 140 mM NaCl, 10 mM Tris-HCl, pH 8) were added to the magnetic particles and mixed well. After 30 minutes, the magnetic particles were captured in the bottom of the well with a magnetic plate, and washed six times with 150 mM NaCl, 20 mM Tris-HCl, 0.02% Tween 20, pH 8. The particles were mixed with alkaline phosphatse substrate (1 mg/mL p-nitrophenyl phosphate in 1 M diethanolamine buffer, 1 mM $MgCl_2$, 0.1 mM $ZnCl_2$, pH 10.4) and incubated at 37° C. for 90 minutes. The $A_{405}$ was measured with a ELISA plate reader (Molecular Devices). As little as 45 pg of oligonucleotide 42-mer was detected. Experimental controls lacking either the 42-mer, or the PDBA or Biotin labeled oligonucleotides did not produce a significant $A_{405}$.

EXAMPLE XII

Preparation of Bioconjugates of General Formula IV

Immobilization of a PDBA-anti-Biotin Conjugate on SHA-Sepharose 4B

One mg of PDBA-anti-Biotin, diluted to 1 mL with tris buffered saline, was applied to small column of SHA-Sepharose 4B (1.0×2.0 cm), and washed extensively with Tris buffered saline. The size of the $A_{280}$ peak of the material not binding to the column indicated that almost all of the PDBA-conjugate was immobilized on the column.

Biotin binding activity of the column was assayed by applying to the column 5 mL of 1 ug/mL biotinylated alkaline phosphatase in Tris buffered saline containing 5 mg/mL bovine serum albumin (BSA). A sample of the peak of the material flowing through the column was collected for comparison of the enzymatic activity with a sample of the alkaline phosphatase dilution applied to column. After applying the sample, the column was washed with 20 mL of buffer. After washing, a very small sample of column material (25 uL liquid containing about 1 uL gel) was collected to measure the enzymatic activity bound to the gel as a result of capture by the immobilized anti-biotin antibody.

The alkaline phosphatase activity was measured by incubating 25 uL of the enzyme samples in 250 uL of 1 mg/mL p-nitrophenylphosphate in 1 M diethanolamine buffer, 1 mM $MgCl_2$, and 0.1 mM $ZnCl_2$, pH 10.4, for 20 minutes and then adding 650 uL of 0.1 M $NaHCO_3$, 10 mM EDTA. Relative to a buffer blank, the $A_{405}$ of the sample applied to the column was 1.57, while the $A_{405}$ of the peak of the material not retained by the column was only 0.042, indicating that virtually all the enzyme conjugate was captured by the column. The small amount of gel assayed produced an $A_{405}$ of 1.30, demonstrating that the enzyme was in fact captured by the column.

EXAMPLE XIII

Preparation of Bioconjugates of General Formula IV

Immobilization of a PDBA-Alkaline Phosphatase Conjugate on SHA-Magnetic Beads

PDBA-conjugated alkaline phosphatase was diluted to 5 ug/mL in Tris buffered saline containing 5 mg/mL bovine serum albumin. Two hundred microliters of diluted PDBA-conjugated enzyme were mixed with 5, 10, or 20 uL of SHA-magnetic beads (Dynal, M280). The enzyme was also mixed with 40 uL of unmodified beads as a control. The beads were mixed gently for 10 minutes on ice, after which the beads were captured with a rare earth magnet and washed 4 times with Tris buffered saline. The beads were then suspended in 250 uL of 1 mg/mL p-nitrophenylphosphate in 1 M diethanolamine buffer, 1 mM $MgCl_2$, and 0.1 mM $ZnCl_2$, pH 10.4, and mixed occasionally at 37° C. for 10 minutes. The reactions were terminated with 750 uL of Tris buffered saline, 5 mM EDTA. The $A_{405}$ relative to a buffer blank was measured to determine the alkaline phosphatase activity bound to the magnetic beads. The control beads produced an $A_{405}$ of only 0.15, while the SHA-magnetic beads produced an $A_{405}$ of 0.62, 0.97, and 1.33 for 5, 10, and 20 uL of beads, respectively, indicating the immobilization of significant amounts of PDBA-AP conjugate on the surface of the beads.

EXAMPLE XIV

Preparation of Bioconjugates of General Formula IV

Capture of a PDBA-Labeled PCR product Hybridized to a Biotin-Labeled Oligonucleotide The wells of an amine-coated polystyrene microwell plate (Corning Costar) were modified with SHA. The plate was backcoated with 5 mg/ML bovine serum albumin (BSA) (300 ul per well in 0.2 M $NaHCO_3$, pH 9.0) for 1 hour at room temperature. The BSA solution was removed by washing the plate five times with ELISA Wash Buffer (150 mM NaCl, 20 mM Tris-HCl, 0.02% Tween 20, pH 8.0).

PDBA-labeled PCR product (2 $\mu$L to 10 $\mu$L) was serially diluted into 200 $\mu$L of 1.5 M NaCl, 150 mM sodium citrate, pH 7 (10× SSC), 0.05% Tween20. One-hundred microliter aliquots of the diluted reactions were added to the microwell plate. The PDBA-labeled PCR product was hybridized with a 5'-biotin labeled 21-mer oligonucleotide for 45 minutes at 40° C. The plate was then washed five times with ELISA Wash Buffer, and 100 ul of Streptavidin-Alkaline Phosphatase (Boehringer Mannheim, 0.2 U/mL in 1 mg/ml BSA, 140 mM NaCl, 10 mM Tris-HCl, pH 8.0) were added to each well and incubated for thirty minutes at room temperature.

The plate was washed 5 times with ELISA Wash Buffer, and 200 ul of p-nitrophenylphosphate (1 mg/mL in diethanolamine, 1 mM $MgCl_2$, 0.1 mM $ZnCl_2$, pH 10.4) were added to the plate and incubated at 37° C. for 30–60 minutes. Less than 90 ng of hybridized product was detected. Experimental controls lacking either the Biotin-oligonucleotide or the PDBA-PCR product did not produce a significant $A_{405}$.

Detection of a PDBA-dUTP PCR product Hybridized to a Biotin-Labeled Oligonucleotide PDBA-dUTP labeled PCR product (10 μL) was diluted into 200 μL of 1.5 M NaCl, 150 mM sodium citrate, pH 7 (10× SSC), 0.05% Tween20 containing 100 ng of a 5'-biotin labeled 21-mer oligonucleotide, and added to a streptavidin plus coated polystyrene microwell plate. Hybridized for 60 minutes at 50° C., and then washed five times in 150 mM NaCl, 20 mM Tris-HCl, 0.02% Tween 20, pH 8 (ELISA Wash Buffer). One hundred microliters of SHA-alkaline phosphatase (1 ug/mL in 1 mg/mL BSA, NaCl, Tris-HCl, pH 8) were added and the plate was incubated for 30 minutes at room temperature. Washed the plate 5 times with ELISA Wash. Alkaline phosphatase substrate was added (1 mg/ml p-nitrophenyl phosphate in 1M diethanolamine buffer, 1 mM $MgCl_2$, 0.1 mM $ZnCl_2$, pH 10.4), and the color developed at 37° C. for 10–60 minutes. A strong yelow color developed indicating the detection of significant amounts of immobilized PDBA-dUTP-labeled PCR product. Experimental controls lacking either the incorporated PDBA-dUTP label, or the Biotin-labeled oligonucleotide did not produce a significant $A_{405}$.

EXAMPLE XV

Preparation of Bioconjugates of General Formula IV Comparison of PBA Bioconjugate with PDBA Bioconjugate Comparison of Binding of PDBA-Alkaline Phosphatase and PBA-Alkalinephosphatase and PBA-Oxime modified SHA Microwell Plates The wells of an amine-coated polystyrene microwell plate (Corning Costar) were modified with SHA. The plate was backcoated with 5 mg/mL bovine serum albumin (BSA) (300 ul per well in 0.2 M $NaHCO_3$, pH 9.0) for 1 hour at room temperature. The BSA solution was removed by washing the plate five times with ELISA Wash Buffer (150 mM NaCl, 20 mM Tris-HCl, 0.02% Tween 20, pH 8.0). The plate was blocked by incubating with PBA-oxime (100 ul per well of 10 mM solution in 40 mM Tris, pH 7.5) at room temperature for 30 minutes. The PBA-oxime solution was removed by washing the plate five times with ELISA wash buffer.

PBA- or PDBA-conjugated alkaline phosphatase (100 ul per well of 1 ug/mL in 0.1 M $NaHCO_3$) was added to the microtiter plate and incubated for 30 minutes at room temperature. The plate was then washed five times with ELISA Wash Bufer, and 200 ul of p-nitrophenylphosphate (1 mg/mL in diethanolamne, 1 mM $MgCl_2$, 0.1 mM $ZnCl_2$, pH 10.4) were added to the plate and incubated at 37° C. for 30–60 minutes. Lower $A_{405}$ was observed in wells containing PBA-alkaline phosphatase than PDBA-alkaline phosphatase consistent with more PDBA-alkaline phosphatase being bound. Experimental controls containing only 0.1 M $NaHCO_3$ or unconjugated alkaline phosphatase did not produce a significant $A_{405}$.

What is claimed is:

1. A reagent having the general formula of General Formula I:

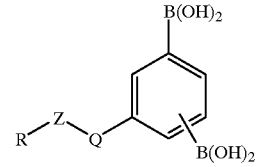

General Formula I wherein group Z comprises a spacer selected from an aliphatic chain up to about 6 carbon equivalents in length, an unbranched aliphatic chain of from about 6 to 18 carbon equivalents in length with at least one of intermediate amide and disulfide moieties, and a polyethylene glycol chain of from about 3 to 12 carbon equivalents in length;

wherein group R is a electrophilic or nucleophilic moiety suitable for reaction of the reagent with a biologically active species; and wherein group Q is one of amide, either and thioether linkages.

2. The reagent of claim 1, wherein group R is preferably selected from one of acrylamido, bromo, bromoacetamido, chloro, chloroacetamido, dithiopyridyl, hydrazide, N-hydorxysuccinimidyl ester, N-hydroxysulfosuccinimidyl ester, imidate ester, imidazolide, iodo, iodoacetamido, maleimido, amino and thiol moieties.

3. The reagent of claim 1, wherein group Z is an unbranched alkyl chain of the general formula $(CH_2)_n$, wherein n=1 to 6.

4. The reagent of claim 1, wherein group Q is selected from one of NHCO, CONH, $NHCOCH_2$, $CONHCH_2$, O, $OCH_2$, S, and $SCH_2$ moieties.

* * * * *